United States Patent
Abe et al.

(10) Patent No.: US 10,626,222 B2
(45) Date of Patent: Apr. 21, 2020

(54) ORGANIC GROUP-MODIFIED ORGANOSILICON RESIN, MAKING METHOD, AND COSMETICS

(71) Applicant: SHIN-ETSU CHEMICAL CO., LTD., Tokyo (JP)

(72) Inventors: Takuya Abe, Annaka (JP); Masayuki Konishi, Tokyo (JP); Chihiro Hayakawa, Tokyo (JP); Masanao Kamei, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 105 days.

(21) Appl. No.: 15/923,478

(22) Filed: Mar. 16, 2018

(65) Prior Publication Data

US 2018/0265642 A1 Sep. 20, 2018

(30) Foreign Application Priority Data

Mar. 17, 2017 (JP) ................. 2017-053099
Nov. 30, 2017 (JP) ................. 2017-230439

(51) Int. Cl.

| | | |
|---|---|---|
| C08G 77/38 | (2006.01) | |
| C08G 77/46 | (2006.01) | |
| A61Q 1/00 | (2006.01) | |
| A61Q 1/06 | (2006.01) | |
| A61Q 1/10 | (2006.01) | |
| A61Q 1/12 | (2006.01) | |
| A61Q 17/04 | (2006.01) | |
| A61K 8/895 | (2006.01) | |
| A61K 8/893 | (2006.01) | |
| A61K 8/894 | (2006.01) | |
| A61Q 19/00 | (2006.01) | |
| C08L 83/12 | (2006.01) | |
| A61K 8/06 | (2006.01) | |
| A61Q 5/00 | (2006.01) | |
| C08G 77/06 | (2006.01) | |
| A61Q 1/08 | (2006.01) | |
| A61Q 5/12 | (2006.01) | |
| A61Q 5/06 | (2006.01) | |
| A61Q 1/02 | (2006.01) | |

(52) U.S. Cl.
CPC .............. *C08G 77/38* (2013.01); *A61K 8/064* (2013.01); *A61K 8/893* (2013.01); *A61K 8/894* (2013.01); *A61K 8/895* (2013.01); *A61Q 1/00* (2013.01); *A61Q 1/06* (2013.01); *A61Q 1/10* (2013.01); *A61Q 1/12* (2013.01); *A61Q 5/00* (2013.01); *A61Q 17/04* (2013.01); *A61Q 19/00* (2013.01); *C08G 77/06* (2013.01); *C08G 77/46* (2013.01); *C08L 83/12* (2013.01); *A61K 2800/10* (2013.01); *A61Q 1/02* (2013.01); *A61Q 1/08* (2013.01); *A61Q 5/06* (2013.01); *A61Q 5/12* (2013.01)

(58) Field of Classification Search
CPC ................................ C08G 77/46; C08G 77/48
See application file for complete search history.

(56) References Cited

U.S. PATENT DOCUMENTS

| | | | | |
|---|---|---|---|---|
| 3,865,544 | A * | 2/1975 | Keil ................... | B01D 19/0404 8/581 |
| 5,225,509 | A | 7/1993 | Heinrich et al. | |
| 5,958,448 | A * | 9/1999 | Ekeland ................... | A61K 8/14 424/450 |
| 6,790,451 | B2 | 9/2004 | Nakanishi | |
| 8,536,109 | B2 * | 9/2013 | Delbrassinne ..... | B01D 19/0404 510/222 |
| 2002/0114771 | A1 * | 8/2002 | Nakanishi .............. | A61K 8/891 424/70.12 |
| 2003/0158363 | A1 | 8/2003 | Nakanishi | |

FOREIGN PATENT DOCUMENTS

| | | |
|---|---|---|
| JP | 61-293903 A | 12/1986 |
| JP | 7-330907 A | 12/1995 |
| JP | 9-143029 A | 6/1997 |
| JP | 2002-179548 A | 6/2002 |
| WO | WO 02/055588 A1 | 7/2002 |

\* cited by examiner

*Primary Examiner* — Marc S Zimmer
(74) *Attorney, Agent, or Firm* — Birch, Stewart, Kolasch & Birch, LLP

(57) ABSTRACT

An organic group-modified organosilicon resin having the average compositional formula (1), which is solid or liquid at 25° C., is suited for use in cosmetics. The resin is able to form an emulsion having a pleasant feel on use, a high internal water phase, and stability over time. In formula (1), a, b, c, d, e, and f are numbers: $0 \le a \le 400$, $0 < b \le 200$, $0 \le c \le 400$, $0 \le d \le 320$, $0 \le e \le 320$, $0 < f \le 1{,}000$, and $0.5 \le (a+b+c)/f \le 1.5$.

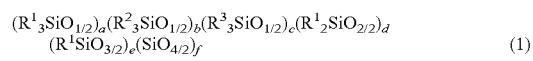

$$(R^1{}_3SiO_{1/2})_a(R^2{}_3SiO_{1/2})_b(R^3{}_3SiO_{1/2})_c(R^1{}_2SiO_{2/2})_d(R^1SiO_{3/2})_e(SiO_{4/2})_f \qquad (1)$$

6 Claims, No Drawings

ORGANIC GROUP-MODIFIED ORGANOSILICON RESIN, MAKING METHOD, AND COSMETICS

CROSS-REFERENCE TO RELATED APPLICATION

This non-provisional application claims priority under 35 U.S.C. § 119(a) on Patent Application Nos. 2017-053099 and 2017-230439 filed in Japan on Mar. 17, 2017 and Nov. 30, 2017, respectively, the entire contents of which are hereby incorporated by reference.

TECHNICAL FIELD

This invention relates to an organic group-modified organosilicon resin and a cosmetic composition comprising the same.

BACKGROUND ART

In the prior art, it is a common practice to blend silicone oil in cosmetics to enhance water repellency for the purpose of sustaining a skin protection effect. In water-in-oil (W/O) emulsion compositions, silicone oil is used as oil ingredient to form light feeling, less sticky and water repellent compositions. Regarding the preparation of such W/O emulsions containing silicone oil, Patent Document 1 discloses the use of an emulsifier such as polyoxyalkylene-modified organopolysiloxane and Patent Document 2 discloses the use of silicone branched polyether-modified silicone which is further increased in compatibility with silicone. However, these straight chain silicone activators alone are difficult to prepare high water content emulsions. When they are blended in high proportions for stabilization, a fresh feel on use is rarely obtainable.

In the field of makeup and sunscreen cosmetics, it is desired from the standpoint of daily use to develop long lasting cosmetics. Outstanding problems for these cosmetics include deterioration of makeup by sweat and sebum secreted from the skin and color transfer due to secondary sticking to cups or the like. One solution is to utilize organosilicon resins because they have water resistance, sebum resistance, water repellency and film-forming ability. The organosilicon resins have essentially silicon-containing three-dimensional structures comprising Q units ($SiO_{4/2}$) and T units ($RSiO_{3/2}$). Owing to many advantages including weather resistance, heat resistance, water repellency, and electric insulation, they are used as intermediate materials destined for pressure-sensitive adhesives, rubber compounds, parting agents, and coating agents. Since the recent discovery of some organosilicon resins having a film-forming ability, the demand for these resins as cosmetic raw materials for foundation, lipstick, eyeshadow, cream, milky lotion and hair-care cosmetics is increasing. For example, a solution of organosilicon resin in cyclic silicone is blended in cosmetics as disclosed in Patent Document 3. However, trimethylsiloxysilicic acid lacks an emulsifying ability.

CITATION LIST

Patent Document 1: JP-A S61-293903
Patent Document 2: JP-A 2002-179548
Patent Document 3: JP-A H09-143029
Patent Document 4: U.S. Pat. No. 5,225,509
Patent Document 5: JP-A H07-330907
Patent Document 6: WO 2000/05588

SUMMARY OF INVENTION

An object of the invention is to provide an organic group-modified organosilicon resin which is able to form an emulsion that has a pleasant feel on use, a high internal water phase, and stability over time when blended in cosmetic compositions, and a cosmetic composition comprising the same.

The inventors have found that an organic group-modified organosilicon resin of the average compositional formula (1) shown below has such a surface activity that when the resin is blended in a cosmetic composition as an emulsifier, the resulting cosmetic composition has a good feel and stability over time. Surprisingly, a W/O emulsion obtained using the organic group-modified organosilicon resin as an emulsifier is an emulsion having a high water content and a large particle size, as compared with emulsions obtained using conventional surfactants such as polyether-modified linear organosiloxanes. The emulsion gives a fresh and light feel and has high stability over time.

In one aspect, the invention provides an organic group-modified organosilicon resin having the average compositional formula (1), the resin being solid or liquid at 25° C.

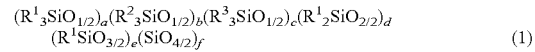  (1)

Herein $R^1$ is each independently a $C_1$-$C_{30}$ alkyl, aryl or aralkyl group or a halogen-, amino- or carboxyl-substituted form thereof. $R^2$ is each independently a polyoxyalkylene group having the formula (2):

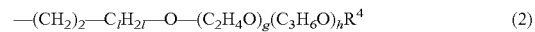  (2)

wherein $R^4$ is a substituted or unsubstituted monovalent hydrocarbon group or hydrogen, l, g and h each are an integer meeting: $0 \le l \le 15$, $0 \le g \le 200$, $0 \le h \le 200$, and $8 \le g+h \le 200$, or $R^1$, at least one $R^2$ is a polyoxyalkylene group of formula (2). $R^3$ is each independently a group having the formula (3), (4), (5) or (6):

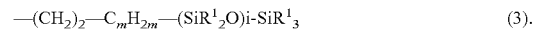  (3).

  (4)

  (5)

  (6)

wherein $R^1$ is as defined above. The subscripts m, i and j1 to j3 each are an integer meeting: $0 \le m \le 5$, $0 \le i \le 500$, $0 \le j1 \le 2$, $0 \le j2 \le 2$, $0 \le j3 \le 2$, or $R^1$, at least one $R^3$ is a group of formula (3), (4), (5) or (6), a, b, c, d, e, and f each are a number meeting: $0 \le a \le 400$, $0 < b \le 200$, $0 \le c \le 400$, $0 \le d \le 320$, $0 \le e \le 320$, $0 < f \le 1,000$, and $0.5 \le (a+b+c)/f \le 1.5$.

Preferably the organosilicon resin has a weight average molecular weight of 1,000 to 100,000 and an HLB of 0.1 to 15 as calculated by the Griffin method.

Preferably, in formula (1), $1 \le c \le 400$, $0.3 \le c/b \le 100$, and $R^3$ contains at least a group of formula (3) wherein $0 < i \le 500$, the organosilicon resin has an HLB of 0.1 to 5.5 as calculated by the Griffin method.

In another aspect, the invention provides a method for preparing the organic group-modified organosilicon resin, comprising the step of effecting hydrosilylation reaction of a hydrosilyl-containing organosilicon resin having the average compositional formula (7), the resin being solid or liquid at 25° C., $$(R^1{}_3SiO_{1/2})_a(H_nR^1{}_{3-n}SiO_{1/2})_{b+c}(R^1{}_2SiO_{2/2})_d(R^1SiO_{3/2})_e(SiO_{4/2})_f \quad (7)$$

wherein $R^1$ is each independently a $C_1$-$C_{30}$ alkyl, aryl or aralkyl group or a halogen-, amino- or carboxyl-substituted form thereof, a, b, c, d, e, and f each are a number meeting: $0 \le a \le 400$, $0 < b \le 200$, $0 \le c \le 400$, $0 \le d \le 320$, $0 \le e \le 320$, $0 < f \le 1,000$, and $0.5 \le (a+b+c)/f \le 1.5$, and n is an integer of 1 to 3, with at least one compound selected from an alkenyl-terminated compound having the formula (8), (9), (10), (11) and (12), and containing compound having the formula (8):

$$CH_2=CH-C_lH_{2l}-O-(C_2H_4O)_g(C_3H_6O)_hR^4 \quad (8)$$

$$CH_2=CHC_mH_{2m}-(SiR^1{}_2O)i-SiR^1{}_3 \quad (9)$$

$$CH_2=CH-C_mH_{2m}-SiR^1{}_{j1}-(OSiR^1{}_3)_{3-j1} \quad (10)$$

$$CH_2=CH-C_mH_{2m}-SiR^1{}_{j1}-(OSiR^1{}_{j2}(OSiR^1{}_3)_{3-j2})_{3-j1} \quad (11)$$

$$CH_2=CH-C_mH_{2m}-SiR^1{}_{j1}-(OSiR^1{}_{j2}(OSiR^1{}_{j3}(OSiR^1{}_3)_{3-j3})_{3-j2})_{3-j1} \quad (12)$$

wherein $R^4$ is a substituted or unsubstituted monovalent hydrocarbon group or hydrogen, l, g and h each are an integer meeting: $0 \le l \le 15$, $0 \le g \le 200$, $0 \le h \le 200$, and $8 \le g+h \le 200$, m, i and j1 to j3 each are an integer meeting: $0 \le m \le 5$, $0 \le i \le 500$, $0 \le j1 \le 2$, $0 \le j2 \le 2$, and $0 \le j3 \le 2$.

Also contemplated herein is a cosmetic composition comprising the organic group-modified organosilicon resin defined above.

Advantageous Effects of Invention

When the organic group-modified organosilicon resin of formula (1) is blended with cosmetic components as an emulsifier, the resulting emulsion has a good feel on use, a high water content, and stability over time. Using the organosilicon resin, satisfactory cosmetic compositions are available.

DESCRIPTION OF PREFERRED EMBODIMENTS

The invention provides an organic group-modified organosilicon resin which is solid or liquid at 25° C. and has the average compositional formula (1).

$$(R^1{}_3SiO_{1/2})_a(R^2{}_3SiO_{1/2})_b(R^3{}_3SiO_{1/2})_c(R^1{}_2SiO_{2/2})_d(R_1SiO_{3/2})_e(SiO_{4/2})_f \quad (1)$$

Herein $R^1$ is each independently a $C_1$-$C_{30}$ alkyl, aryl or aralkyl group or a halogen-, amino- or carboxyl-substituted form thereof. $R^2$ is each independently a polyoxyalkylene group having the formula (2):

$$-(CH_2)_2-C_lH_{2l}-O-(C_2H_4O)_g(C_3H_6O)_hR^4 \quad (2)$$

wherein $R^4$ is a substituted or unsubstituted monovalent hydrocarbon group or hydrogen, l, g and h each are an integer meeting: $0 \le l \le 15$, $0 \le g \le 200$, $0 \le h \le 200$, and $8 \le g+h \le 200$, or $R^1$, and at least one $R^2$ is a polyoxyalkylene group of formula (2). $R^3$ is each independently a group having the formula (3), (4), (5) or (6):

$$-(CH_2)_2-C_mH_{2m}-(SiOR^1{}_2)_i-SiR^1{}_3 \quad (3)$$

$$-(CH_2)_2-C_mH_{2m}-SiR^1{}_{j1}-(OSiR^1{}_3)_{3-j1} \quad (4)$$

$$-(CH_2)_2-C_mH_{2m}-SiR^1{}_{j1}-(OSiR^1{}_{j2}(OSiR^1{}_3)_{3-j2})_{3-j1} \quad (5)$$

$$-(CH_2)_2-C_mH_{2m}-SiR^1{}_{j1}-(OSiR^1{}_{j2}(OSiR^1{}_{j3}(OSiR^1{}_3)_{3-j3})_{3-j2})_{3-j1} \quad (6)$$

wherein $R^1$ is as defined above, m, i and j1 to j3 each are an integer meeting: $0 \le m \le 5$, $0 \le i \le 500$, $0 \le j1 \le 2$, $0 \le j2 \le 2$, $0 \le j3 \le 2$, or $R^1$, and at least one $R^3$ is a group of formula (3), (4), (5) or (6). The subscripts a, b, c, d, e, and f each are a number meeting: $0 \le a \le 400$, $0 < b \le 200$, $0 \le c \le 400$, $0 \le d \le 320$, $0 \le e \le 320$, $0 < f \le 1,000$, and $0.5 \le (a+b+c)/f \le 1.5$.

In formula (1), $R^1$ is each independently a $C_1$-$C_{30}$ alkyl, aryl or aralkyl group or a halogen-, amino- or carboxyl-substituted form of $C_1$-$C_{30}$ alkyl, aryl or aralkyl group. Of groups $R^1$, preferred are alkyl, aryl, aralkyl, fluorine-substituted alkyl, chlorine-substituted alkyl, amino-substituted alkyl, and carboxyl-substituted alkyl groups of 1 to 10 carbon atoms. Typical groups include methyl, ethyl, propyl, butyl, pentyl, cyclopentyl, cyclohexyl, phenyl, tolyl, trifluoropropyl, heptadecafluorodecyl, chloropropyl, and chlorophenyl. Inter alia, $C_1$-$C_5$ alkyl groups, phenyl, and trifluoropropyl are more preferred.

The subscript "a" is a number in the range: $0 \le a \le 400$, preferably $1 \le a \le 100$, more preferably $1 \le a \le 50$. If "a" is more than 400, then a resin becomes less hydrophilic and is difficult to form a stable emulsion. The subscript "b" is a number in the range: $0 < b \le 200$, preferably $1 \le b \le 100$, more preferably $1 \le b \le 50$. If b is more than 200, then a resin becomes extremely hydrophilic, with a lack of stability. The subscript "c" is a number in the range: $0 \le c \le 400$, preferably $1 \le c \le 100$, more preferably $1 \le c \le 50$. If c is more than 400, then a resin becomes less hydrophilic, with a lack of stability. If c=0, a resin has a poor emulsifying ability, posing a risk of difficulty to form a stable emulsion in the case of an oil mixture of ester oil and hydrocarbon oil. For this reason, $0 < c$ is preferred. The subscripts d, e and f are numbers in the range: $0 \le d \le 320$, $0 \le e \le 320$, $0 < f \le 1,000$, and $0.5 \le (a+b+c)/f \le 1.5$, preferably $0.7 \le (a+b+c)/f \le 1.2$.

$R^2$ is each independently a polyoxyalkylene group having the formula (2) or $R^1$, $$-(CH_2)_2-C_lH_{2l}-O-(C_2H_4O)_g(C_3H_6O)_hR^4 \quad (2)$$

wherein $R^4$ is a substituted or unsubstituted monovalent hydrocarbon group or hydrogen, l, g and h each are an integer meeting: $0 \le l \le 15$, $0 \le g \le 200$, $0 \le h \le 200$, and $8 \le g+h \le 200$, and at least one $R^2$ is a polyoxyalkylene group of formula (2). $R^1$ is as defined and exemplified above. $R^4$ is a substituted or unsubstituted monovalent hydrocarbon group or hydrogen. The subscript l is an integer in the range: $0 \le l \le 15$, preferably $0 \le l \le 2$. The subscript g is an integer in the range: $0 \le g \le 200$, preferably $1 \le g \le 100$, more preferably $8 \le g \le 50$. If g is more than 200, a resin becomes extremely hydrophilic, with a lack of stability. The subscript h is an integer in the range: $0 \le h \le 200$, preferably $0 \le h \le 100$, more preferably $8 \le h \le 50$. If h is more than 200, a resin becomes extremely hydrophilic, with a lack of stability. The sum of g and h is $8 \le g+h \le 200$, preferably $8 \le g+h \le 100$, more preferably $8 \le g+h \le 50$. If g+h is less than 8, a resin becomes less hydrophilic and less emulsifying, with a lack of stability. A ratio $g/h \ge 1$ is desired for the purpose of imparting sufficient hydrophilicity in order to form a W/O emulsion whereas $g/h \le 1$ is desired for the purpose of imparting sufficient hydrophobicity in order to form an O/W emulsion. Where the polyoxyalkylene section consists of both ethylene oxide units and propylene oxide units, it may be a block or random copolymer of both the units.

$R^3$ is each independently a group having the formula (3), (4), (5) or (6), or $R^1$,

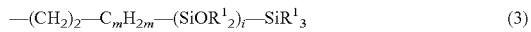
$$—(CH_2)_2—C_mH_{2m}—(SiOR^1_2)_i—SiR^1_3 \quad (3)$$

$$—(CH_2)_2—C_mH_{2m}—SiR^1_{j1}—(OSiR^1_3)_{3-j1} \quad (4)$$

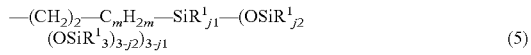
$$—(CH_2)_2—C_mH_{2m}—SiR^1_{j1}—(OSiR^1_{j2}(OSiR^1_3)_{3-j2})_{3-j1} \quad (5)$$

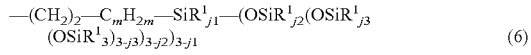
$$—(CH_2)_2—C_mH_{2m}—SiR^1_{j1}—(OSiR^1_{j2}(OSiR^1_{j3}(OSiR^1_3)_{3-j3})_{3-j2})_{3-j1} \quad (6)$$

wherein $R^1$ is each independently a $C_1$-$C_{30}$ alkyl, aryl or aralkyl group or a halogen-, amino- or carboxyl-substituted form thereof, m, i and j1 to j3 each are an integer meeting: $0 \leq m \leq 5$, $0 \leq i \leq 500$, $0 \leq j1 \leq 2$, $0 \leq j2 \leq 2$, $0 \leq j3 \leq 2$, and at least one $R^3$ is a group of formula (3), (4), (5) or (6). $R^1$ is as defined and exemplified above. The subscript m is an integer in the range: $0 \leq m \leq 5$, preferably $0 \leq m \leq 2$. The subscript i is an integer in the range: $0 \leq i \leq 500$, preferably $0 \leq i \leq 100$, more preferably $1 \leq i \leq 50$. If i exceeds 500, a resin becomes less hydrophilic, with a lack of stability.

From the standpoint of reaction of vinyl with hydrogenpolysiloxane, the synthesis of a unit having formula (3) prefers m=0. If i exceeds 500, there arise problems such as a lack of reactivity with the backbone, hydrogenpolysiloxane. For this reason, i is preferably in the range defined above. From the standpoint of reaction of vinyl with hydrogenpolysiloxane, the synthesis of a unit having formula (4), (5) or (6) prefers m=0.

When the following conditions are met, that is, in formula (1), $0<b \leq 200$, $1 \leq c \leq 400$, $0.3 \leq c/b \leq 100$, in formula (2), $0 \leq g \leq 200$, $0 \leq h \leq 200$, and $8 \leq g+h \leq 200$, $R^3$ contains at least a group of formula (3), in formula (3), $0<i \leq 500$, and an HLB value as calculated by the Griffin method is from 0.1 to 5.5, there is obtained an organic group-modified organosilicon resin which may be utilized as a W/O emulsifier and has a very high solubility in silicone oil.

Preparation Method

The organic group-modified organosilicon resins may be synthesized by any well-known prior art formulations. For example, an organic group may be introduced by reacting a chlorosilane such as $R^3SiCl$ with surface silanol groups on an organosilicon resin for silylation. However, it is difficult to completely control a silanol group content on the organosilicon resin surface, which in turn makes it difficult to precisely control the amount of modifying organic groups. Since strong acid generates during silylation reaction, there is a possibility to cleave bonds in the organosilicon resin. Also, organic functional groups can be introduced in one pot by co-condensation of two types of alkoxysilanes each consisting of Q units ($SiO_{4/2}$) and T units ($RSiO_{3/2}$) wherein some R are organic functional groups. However, since two types of alkoxysilanes are different in hydrolysis, it is difficult to produce an organosilicon resin in which Q units and T units are uniformly distributed. For this reason, an organic group-modified organosilicon resin is generally synthesized by hydrosilylation reaction of an organosilicon resin having a hydrosilyl group as a reactive site with a compound terminated with an alkenyl group (carbon-carbon unsaturated bond).

According to the invention, the organic group-modified organosilicon resin is prepared by a method involving hydrosilylation reaction of a hydrosilyl-containing organosilicon resin having the average compositional formula (7):

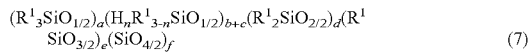
$$(R^1_3SiO_{1/2})_a(H_nR^1_{3-n}SiO_{1/2})_{b+c}(R^1_2SiO_{2/2})_d(R^1SiO_{3/2})_e(SiO_{4/2})_f \quad (7)$$

wherein $R^1$ is each independently a $C_1$-$C_{30}$ alkyl, aryl or aralkyl group or a halogen-, amino- or carboxyl-substituted form thereof, a, b, c, d, e, and f each are a number meeting: $0 \leq a \leq 400$, $0<b \leq 200$, $0 \leq c \leq 400$, $0 \leq d \leq 320$, $0 \leq e \leq 320$, $0<f \leq 1,000$, and $0.5 \leq (a+b+c)/f \leq 1.5$, and n is an integer of 1 to 3, the resin being composed essentially of Q units, M units and ($H_nR^1_{3-n}Si_{1/2}$) units, and being solid or liquid at 25° C., with at least one compound selected from an alkenyl-terminated compound having the formula (8), (9), (10), (11) and (12), and containing compound having the formula (8):

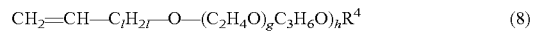
$$CH_2=CH—C_lH_{2l}—O—(C_2H_4O)_g(C_3H_6O)_hR^4 \quad (8)$$

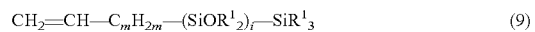
$$CH_2=CH—C_mH_{2m}—(SiOR^1_2)_i—SiR^1_3 \quad (9)$$

$$CH_2=CH—C_mH_{2m}—SiR^1_{j1}—(OSiR^1_3)_{3-j1} \quad (10)$$

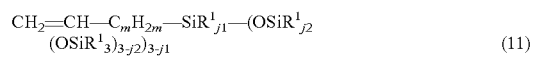
$$CH_2=CH—C_mH_{2m}—SiR^1_{j1}—(OSiR^1_{j2}(OSiR^1_3)_{3-j2})_{3-j1} \quad (11)$$

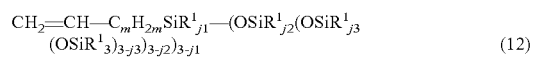
$$CH_2=CH—C_mH_{2m}SiR^1_{j1}—(OSiR^1_{j2}(OSiR^1_{j3}(OSiR^1_3)_{3-j3})_{3-j2})_{3-j1} \quad (12)$$

wherein $R^4$ is a substituted or unsubstituted monovalent hydrocarbon group or hydrogen, l, g and h each are an integer meeting: $0 \leq l \leq 15$, $0 \leq g \leq 200$, $0 \leq h \leq 200$, and $8 \leq g+h \leq 200$, m, i and j1 to j3 each are an integer meeting: $0 \leq m \leq 5$, $0 \leq i \leq 500$, $0 \leq j1 \leq 2$, $0 \leq j2 \leq 2$, and $0 \leq j3 \leq 2$. The hydrosilylation reaction is effected in the presence of a platinum or rhodium catalyst, for example. The definition and preferred ranges of $R^1$, b, c, d, e, f, $R^4$, l, g, h, m, i, j1, j2 and j3 are as described above.

While the hydrosilyl-containing organosilicon resin having formula (7) is solid or liquid at 25° C., it is preferably diluted with an organic solvent prior to use. For dilution, a solvent having a boiling point higher than the reflux temperature during hydrolysis (described later) is preferably used.

Examples of the organic solvent used for dilution include cyclic organopolysiloxanes such as octamethylcyclotetrasiloxane, decamethylcyclopentasiloxane, and dodecamethylcyclohexasiloxane; aromatic hydrocarbons such as toluene and xylene; ketone solvents such as acetone, methyl ethyl ketone, diethyl ketone and methyl isobutyl ketone; aliphatic hydrocarbons such as hexane, heptane, octane and cyclohexane; and aliphatic alcohols such as methanol, ethanol, 1-propanol, 2-propanol, 1-butanol, 2-methyl-1-propanol, 2-butanol, 2-methyl-2-propanol, 1-pentanol, 2-methylbutanol, 2-pentanol, 1-hexanol, 2-methylpentanol, 1-heptanol, 1-octanol, 1-nonanol, 1-decanol, phenol, benzyl alcohol, ethylene glycol, and 1,2-propylene glycol. From the standpoints of shelf stability and non-volatility, octamethylcyclotetrasiloxane and decamethylcyclopentasiloxane are preferred.

The hydrosilyl-containing organosilicon resin having formula (7) is prepared by effecting hydrolysis of a mixture of at least one member selected from organosilicon compounds having the general formulae (13) and (14), at least one member selected from hydrosilyl-containing organosilicon compounds having the general formulae (15) and (16), and at least one member selected from a hydrolyzable silane having the general formula (17), a partial hydrolytic condensate thereof, and a metal salt thereof, in the presence of an acid catalyst, adding a base catalyst in an amount in excess of the molar equivalent of the acid catalyst for neutralization, and thereafter effecting condensation.

$$R^1_3SiOSiR^1_3 \quad (13)$$

$$R^1_3SiX^1 \quad (14)$$

$$H_nR^1_{(3-n)}SiOSiR^1_{(3-n)}H_n \quad (15)$$

$$H_nR^1_{(3-n)}SiX^2 \tag{16}$$

$$SiX^3_4 \tag{17}$$

Herein $R^1$ is each independently a $C_1$-$C_{30}$ alkyl, aryl or aralkyl group or a halogen-, amino- or carboxyl-substituted form thereof, $X^1$ and $X^2$ each are a hydrolyzable functional group, n is $1 \leq n \leq 3$, and $X^3$ is a hydrolyzable functional group.

In formulae (13), (14), (15) and (16), $R^1$ is as defined and exemplified above.

In formula (14), $X^1$ is a silicon-bonded hydrolyzable functional group, examples of which include halogen atoms such as chlorine and bromine, alkoxy groups such as methoxy, ethoxy, propoxy and butoxy, alkenoxy groups, acyloxy groups, amide groups, and oxime groups. From the standpoints of availability and hydrolysis rate, methoxy, ethoxy and chlorine are preferred.

In formula (16), $X^2$ is a silicon-bonded hydrolyzable functional group, examples of which include halogen atoms such as chlorine and bromine, alkoxy groups such as methoxy, ethoxy, propoxy and butoxy, alkenoxy groups, acyloxy groups, amide groups, and oxime groups. From the standpoints of availability and hydrolysis rate, methoxy, ethoxy and chlorine are preferred.

In formula (17), $X^3$ is a silicon-bonded hydrolyzable functional group, examples of which include halogen atoms such as chlorine and bromine, alkoxy groups such as methoxy, ethoxy, propoxy and butoxy, alkenoxy groups, acyloxy groups, amide groups, and oxime groups, with the alkoxy groups being preferred. From the standpoints of availability and hydrolysis rate, methoxy and ethoxy are more preferred. A plurality of hydrolyzable groups $X^3$ in the molecule may be identical or different.

Examples of the organosilicon compound having formula (13) include 1,1,1,3,3,3-hexamethyldisiloxane, 1,1,1,3,3,3-hexaphenyldisiloxane, 1,1,3,3-tetramethyl-1,3-divinyldisiloxane, 1,1,1,3,3,3-hexaethyldisiloxane, 1,1,1,3,3,3-hexavinyldisiloxane, 1,1,1,3,3-pentavinylmethyldisiloxane, 1,1,1,3,3-n-octylpentamethyldisiloxane, 1,1,1,3,3-chloromethylpentamethyldisiloxane, 1,1,3,3-tetramethyl-1,3-diallyldisiloxane, 1,3-dimethyl-1,1,3,3-tetravinyldisiloxane. Inter alia, 1,1,1,3,3,3-hexamethyldisiloxane and 1,1,1,3,3,3-hexaphenyldisiloxane are preferred.

Examples of the organosilicon compound having formula (14) include trimethylchlorosilane, triethylchlorosilane, ethyldimethylchlorosilane, trivinylchlorosilane, dimethylvinylchlorosilane, triphenylchlorosilane, dimethylphenylchlorosilane, methyldiphenylchlorosilane, trimethylmethoxysilane, trimethylethoxysilane, triethylmethoxysilane, triethylethoxysilane, triphenylmethoxysilane, and triphenylethoxysilane. Inter alia, trimethylchlorosilane and trimethylthoxysilane are preferred.

Examples of the hydrosilyl-containing organosilicon compound having formula (15) include 1,1,3,3-tetramethyldisiloxane and 1,1,1,3,3-pentamethyldisiloxane. Inter alia, 1,1,3,3-tetramethyldisiloxane is preferred. It is noted that in formulae (15) and (16), n is an integer of 1 to 3, and in formula (15), n suffixed to H and $R^1$ bonded to one silicon atom may be identical with or different from n suffixed to H and $R^1$ bonded to the other silicon atom.

Examples of the hydrosilyl-containing organosilicon compound having formula (16) include dimethylchlorosilane, diphenylchlorosilane, dimethylmethoxysilane, and dimethylethoxysilane. Inter alia, dimethylchlorosilane and dimethylmethoxysilane are preferred.

Examples of the hydrolyzable silane having formula (17) include tetrachlorosilane, tetramethoxysilane, and tetraethoxysilane. Suitable partial hydrolytic condensates of the hydrolyzable silane include tetramethoxysilane condensates and tetraethoxysilane condensates. Suitable metal salts of the hydrolyzable silane include water glass, sodium silicate, and potassium silicate. Inter alia, tetraethoxysilane and tetraethoxysilane condensates are preferred.

Prior to hydrolysis of a mixture of at least one member selected from organosilicon compounds having formulae (13) and (14), at least one member selected from hydrosilyl-containing organosilicon compounds having formulae (15) and (16), and at least one member selected from a hydrolyzable silane having formula (17), a partial hydrolytic condensate thereof, and a metal salt thereof, in the presence of an acid catalyst, or prior to second hydrolysis following the hydrolysis, at least one member selected from organosilicon compounds having the general formulae (18) and (19) may be further added.

$$R^1SiX^4_3 \tag{18}$$

$$R^1_2SiX^5_2 \tag{19}$$

Herein $R^1$ is each independently a $C_1$-$C_{30}$ alkyl, aryl or aralkyl group or a halogen-, amino- or carboxyl-substituted form thereof, $X^4$ and $X^1$ each are a hydrolyzable functional group.

In formulae (18) and (19), $R^1$ is as defined and exemplified above.

In formula (18), $X^4$ is a silicon-bonded hydrolyzable functional group, examples of which include halogen atoms such as chlorine and bromine, alkoxy groups such as methoxy, ethoxy, propoxy and butoxy, alkenoxy groups, acyloxy groups, amide groups, and oxime groups. From the standpoints of availability and hydrolysis rate, methoxy, ethoxy and chlorine are preferred. A plurality of hydrolyzable groups $X^4$ in the molecule may be identical or different.

In formula (19), $X^1$ is a silicon-bonded hydrolyzable functional group, examples of which include halogen atoms such as chlorine and bromine, alkoxy groups such as methoxy, ethoxy, propoxy and butoxy, alkenoxy groups, acyloxy groups, amide groups, and oxime groups. From the standpoints of availability and hydrolysis rate, methoxy, ethoxy and chlorine are preferred. A plurality of hydrolyzable groups $X^1$ in the molecule may be identical or different.

Examples of the organosilicon compound having formula (18) include methyltrimethoxysilane, methyltriethoxysilane, ethyltrimethoxysilane, pentyltriethoxysilane, phenyltriethoxysilane, benzyltriethoxysilane, chloropropyltriethoxysilane, bromopropyltriethoxysilane, cyclohexyltrimethoxysilane, trifluoropropyltrimethoxysilane, and methyltrichlorosilane. Inter alia, methyltrimethoxysilane, methyltriethoxysilane, and methyltrichlorosilane are preferred.

Examples of the organosilicon compound having formula (19) include dimethyldimethoxysilane, dimethyldiethoxysilane, diethyldimethoxysilane, dipentyldiethoxysilane, diphenyldiethoxysilane, dibenzyldiethoxysilane, dichloropropyldiethoxysilane, dibromopropyldiethoxysilane, dicyclohexyldimethoxysilane, difluoropropyldimethoxysilane, and dimethyldichlorosilane. Inter alia, dimethyldimethoxysilane, dimethyldiethoxysilane, and dimethyldichlorosilane are preferred.

Described below is one exemplary method for preparing the hydrosilyl-containing organosilicon resin used as the starting material in the inventive method. A reactor is charged with a solvent, typically organic solvent, and hydrolytic reactants (i.e., a mixture of at least one member selected from organosilicon compounds having formulae (13) and (14), at least one member selected from hydrosilyl-containing organosilicon compounds having formulae (15) and (16), and at least one member selected from a hydrolyzable silane having formula (17), a partial hydrolytic condensate thereof, and a metal salt thereof), an acid is to added as catalyst, and with stirring, water is added dropwise. Alternatively, the organic solvent may be added at the end of dropwise addition of water. The addition of the acid catalyst is essential since hydrolysis is preferably carried out under acidic conditions.

During dropwise addition of water, the temperature is preferably kept in a range of 0 to 80° C., more preferably 0 to 50° C. This temperature range is effective for suppressing the heat generated by hydrolytic reaction of hydrolytic reactants in the system. An appropriate amount of water added is 0.6 to 2 moles, preferably 1.0 to 1.8 moles per mole of hydrolyzable functional groups (typically alkoxy groups). A molar ratio within this range ensures to prevent hydrosilyl groups from deactivation.

While the solvent is used in hydrolytic reaction, an organic solvent is appropriate for keeping the reaction system uniform during hydrolytic reaction and for preventing the system from increasing its viscosity to decelerate the reaction rate. An organic solvent having a boiling point higher than the reflux temperature during hydrolysis is preferably used.

Suitable organic solvents include cyclic organopolysiloxanes such as octamethylcyclotetrasiloxane, decamethylcyclopentasiloxane, and dodecamethylcyclohexasiloxane; aromatic hydrocarbons such as toluene and xylene; ketone solvents such as acetone, methyl ethyl ketone, diethyl ketone, and methyl isobutyl ketone; and aliphatic hydrocarbons such as hexane, heptane, octane and cyclohexane.

An alcohol solvent of 1 to 10 carbon atoms may be used in admixture with the above. Suitable alcohols include methanol, ethanol, 1-propanol, 2-propanol, 1-butanol, 2-methyl-1-propanol, 2-butanol, 2-methyl-2-propanol, 1-pentanol, 2-methylbutanol, 2-pentanol, 1-hexanol, 2-methylpentanol, 1-heptanol, 1-octanol, 1-nonanol, 1-decanol, phenol, benzyl alcohol, ethylene glycol, and 1,2-propylene glycol. Since the alcohol solvent undergoes alcohol exchange reaction with a hydrolyzable group such as alkoxy, the use of long-chain alcohol solvent may determine the rate of hydrolytic reaction. Thus methanol, ethanol, 1-propanol and 2-propanol are preferred.

The solvent is preferably used in an amount of 1 to 80% by weight, more preferably 5 to 50% by weight of the overall system. As long as the amount of the solvent is in this range, the reaction system is kept uniform and allows for efficient progress of reaction.

Examples of the acid catalyst include hydrochloric acid, sulfuric acid, sulfurous acid, fuming sulfuric acid, oxalic acid, p-toluenesulfonic acid, methanesulfonic acid, trifluoromethanesulfonic acid, phosphoric acid, formic acid, acetic acid, propionic acid, benzoic acid, and citric acid. The acid catalyst may be used in a small amount, preferably of 0.001 to 10% by weight of the overall system.

Once water is added dropwise, the system is heated, for example, at a temperature of 50 to 150° C., preferably 80 to 120° C. for about 2 to 8 hours to effect hydrolytic reaction. The heating temperature may be kept below the boiling point of the hydrosilyl-containing organic compound for further suppressing the deactivation of hydrosilyl groups.

Once the hydrolytic reactants are hydrolyzed in the presence of an acid catalyst as described above, the system is cooled down to a temperature of 10 to 100° C., preferably 10 to 60° C., more preferably 10 to 30° C., most preferably 25° C.

After the hydrolysis, the reaction system is neutralized at 10 to 40° C. with a base catalyst, which is selected from alkali metal carbonates, alkali metal hydrogencarbonates, and alkali metal hydroxides. Use of a strong base catalyst in combination with a weak base catalyst is effective for further suppressing the deactivation of hydrosilyl groups and for promoting condensation reaction to an organosilicon resin. Suitable strong base catalysts include lithium hydroxide, sodium hydroxide, potassium hydroxide, calcium hydroxide and barium hydroxide. Suitable weak base catalysts include sodium carbonate, calcium carbonate and sodium hydrogencarbonate. The combination of strong base catalyst and weak base catalyst which is preferred from the standpoint of molecular weight buildup is a combination of sodium hydroxide and calcium carbonate, which ensures to produce a hydrosilyl-containing organosilicon resin having a high molecular weight.

The amount of the base catalyst used should be larger than the molar equivalent of the acid catalyst. When the system is neutralized with an amount of the base catalyst in excess of the equivalent of the acid catalyst, condensation reaction to organosilicon resin preferentially takes place, resulting in a molecular weight buildup, i.e., a hydrosilyl-containing organosilicon resin having a high molecular weight. Specifically the amount of the base catalyst used is 1.1 to 3.0 molar equivalents per molar equivalent of the acid catalyst. The amount of the base catalyst in this range ensures that condensation reaction to a hydrosilyl-containing organosilicon resin preferentially takes place, resulting in an organosilicon resin having a desired molecular weight.

After the neutralization, the alcohol formed, the solvent and excess water may be removed by heating at 95 to 120° C. under atmospheric or reduced pressure. After it is confirmed that the alcohol, solvent and excess water are removed, the system is heated, for example, at 120 to 150° C. for about 2 to 5 hours to promote condensation reaction. In this way, a hydrosilyl-containing organosilicon resin is obtained.

In the above-described method for preparing the hydrosilyl-containing organosilicon resin, the total amount of compounds having formulae (13), (14), (15) and (16) and the amount of $SiO_{4/2}$ units in the compound having formula (17) are such that a molar ratio of $\{(13)+(14)+(15)+(16)\}:(17)$ is preferably from 0.3:1 to 2:1, more preferably from 0.6:1 to 1.3:1. The total amount of compounds having formulae (13) and (14) and the total amount of compounds having formulae (15) and (16) are such that a molar ratio of $\{(13)+(14)\}:\{(15)+(16)\}$ is preferably from 0.3:1.0 to 2.0:1.0, more preferably from 0.6:1.0 to 1.3:1.0. These ranges ensure that the amount of hydrosilyl groups in the hydrosilyl-containing organosilicon resin is accurately and quantitatively varied. According to the invention, the amount of hydrosilyl groups in the hydrosilyl-containing organosilicon resin is quantitatively varied by changing the charge of the compound having formula (15) and/or (16).

In an alternative embodiment of the method for preparing the hydrosilyl-containing organosilicon resin, a mixture of at least one member selected from organosilicon compounds having formulae (13) and (14), and at least one member selected from a hydrolyzable silane having formula (17), a partial hydrolytic condensate thereof, and a metal salt thereof is hydrolyzed in the presence of an acid catalyst, after which at least one member selected from hydrosilyl-containing organosilicon compounds having formulae (15) and (16) is added dropwise to the mixture.

This is followed by hydrolysis again (sometimes referred to as "second hydrolysis"). At this point, the system is preferably heated at a temperature below the boiling point of the hydrosilyl-containing organic compound, preferably 40 to 150° C., more preferably 40 to 120° C. for about 2 to 8 hours for the second hydrolysis to take place. This temperature range for hydrolysis is effective for preventing hydrosilyl groups from deactivation.

In the method for preparing the hydrosilyl-containing organosilicon resin, some hydrosilyl groups can be deactivated according to the following reaction scheme (20).

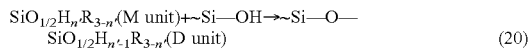

$$SiO_{1/2}H_nR_{3-n}(M\ unit)+\sim Si-OH\rightarrow \sim Si-O-SiO_{1/2}H_{n'-1}R_{3-n'}(D\ unit) \quad (20)$$

Herein R is a $C_1$-$C_{10}$ monovalent hydrocarbon group, and n' is an integer of 1 to 3.

However, the potential of side reaction according to scheme (20) may be suppressed by tailoring the addition sequence of reactants, that is, when hydrolysis of a mixture of an organosilicon compound having formula (13) and/or (14) and a hydrolyzable silane having formula (17) is followed by addition of a hydrosilyl-containing organosilicon compound having formula (15) and/or (16) and second hydrolysis. The potential of side reaction may be minimized by adjusting the amounts of reactants and the type of catalyst.

When the hydrosilyl-containing organosilicon resin is prepared in this way, the amount of hydrosilyl groups introduced into the organosilicon resin may be easily adjusted by changing the amount of hydrosilyl-containing organosilicon compound charged, indicating that a large amount of hydrosilyl groups may be introduced into the organosilicon resin. Furthermore, by changing the amounts of hydrolyzable reactants, the type and amount of acid catalyst, reaction temperature, reaction time, the amount of solvent, and addition mode, the organosilicon resin may be adjusted in molecular weight distribution and form. That is, a hydrosilyl-containing organosilicon resin suited for a particular application may be prepared.

The hydrosilyl-containing organosilicon resin thus obtained is represented by the average compositional formula (7), is composed of Q units ($SiO_{4/2}$) and M units ($R^1_3SiO_{1/2}$ and $H_nR^1_{3-n}SiO_{1/2}$) as essential units and D units ($R^1_2SiO_{2/2}$) and T units ($R^1SiO_{3/2}$) as optional units, and takes solid or liquid form at room temperature when solvent-free. For example, MQ resin, MTQ resin, MDQ resin, and MDTQ resin are included. The organosilicon resin should preferably have a weight average molecular weight (Mw) of 2,000 to 30,000, with a Mw of 3,000 to 15,000 being more preferred from the standpoints of performance and efficient filtration or operation. It is noted that Mw is measured versus polystyrene standards by gel permeation chromatography (GPC).

Exemplary Preparation of Organosilicon Resin

Described below is one exemplary embodiment of the method for preparing the organic group-modified organosilicon resin according to the invention.

As alluded to previously, the organic group-modified organosilicon resin may be prepared, for example, by the step of hydrosilylation reaction of a hydrosilyl-containing organosilicon resin having the average compositional formula (7):

$$(R^1_3SiO_{1/2})_a(H_nR^1_{3-n}SiO_{1/2})_{b+c}(R^1_2SiO_{2/2})_d(R^1SiO_{3/2})_e(SiO_{4/2})_f \quad (7)$$

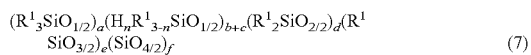

wherein $R^1$ is each independently a $C_1$-$C_{30}$ alkyl, aryl or aralkyl group or a halogen-, amino- or carboxyl-substituted form thereof, a, b, c, d, e, and f each are a number meeting: 0≤a≤400, 0<b≤200, 0≤c≤400, 0≤d≤320, 0≤e≤320, 0<f≤1,000, and 0.5≤(a+b+c)/f≤1.5, and n is an integer of 1 to 3, the resin being solid or liquid at 25° C., with at least one compound selected from an alkenyl-terminated compound having the formula (8), (9), (10), (11) and (12), and containing compound having the formula (8):

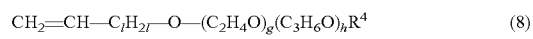

$$CH_2=CH-C_lH_{2l}-O-(C_2H_4O)_g(C_3H_6O)_hR^4 \quad (8)$$

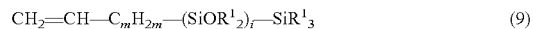

$$CH_2=CH-C_mH_{2m}-(SiOR^1_2)_i-SiR^1_3 \quad (9)$$

$$CH_2=CH-C_mH_{2m}-SiR^1_{j1}-(OSiR^1_3)_{3-j1} \quad (10)$$

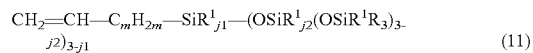

$$CH_2=CH-C_mH_{2m}-SiR^1_{j1}-(OSiR^1_{j2}(OSiR^1R_3)_{3-j2})_{3-j1} \quad (11)$$

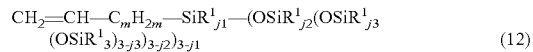

$$CH_2=CH-C_mH_{2m}-SiR^1_{j1}-(OSiR^1_{j2}(OSiR^1_{j3}(OSiR^1_3)_{3-j3})_{3-j2})_{3-j1} \quad (12)$$

wherein $R^4$ is a substituted or unsubstituted monovalent hydrocarbon group or hydrogen, l, g and h each are an integer meeting: 0≤l≤15, 0≤g≤200, 0≤h≤200, and 8≤g+h≤200, m, i and j1 to j3 each are an integer meeting: 0≤m≤5, 0≤i≤500, 0≤j1≤2, 0≤j2≤2, and 0≤j3≤2. The hydrosilyl-containing organosilicon resin having formula (7) is combined with the polyoxyalkylene compound having formula (8) (essential compound) and organopolysiloxane compound having formula (9), (10), (11) or (12) such that a molar ratio of hydrosilyl groups to terminal unsaturated groups (hydrosilyl groups/terminal unsaturated groups) may range preferably from 0.5/1 to 2.0/1, more preferably from 0.8/1 to 1.2/1.

The hydrosilylation or addition reaction is preferably carried out in the presence of a platinum or rhodium catalyst. Suitable catalysts include chloroplatinic acid, alcohol-modified chloroplatinic acid, and chloroplatinic acid-vinyl siloxane complexes. The catalyst is preferably used in such an amount as to provide 50 ppm or less, more preferably 20 ppm or less of platinum or rhodium because an excess of the catalyst can color the resin.

If desired, the addition reaction may be carried out in an organic solvent. Suitable organic solvents include cyclic organopolysiloxanes such as octamethylcyclotetrasiloxane, decamethylcyclopentasiloxane, and dodecamethylcyclohexasiloxane; aromatic hydrocarbons such as toluene and xylene; ketone solvents such as acetone, methyl ethyl ketone, diethyl ketone and methyl isobutyl ketone; aliphatic hydrocarbons such as hexane, heptane, octane and cyclohexane; and aliphatic alcohols such as methanol, ethanol, 1-propanol, 2-propanol, 1-butanol, 2-methyl-1-propanol, 2-butanol, 2-methyl-2-propanol, 1-pentanol, 2-methylbutanol, 2-pentanol, 1-hexanol, 2-methylpentanol, 1-heptanol, 1-octanol, 1-nonanol, 1-decanol, phenol, benzyl alcohol, ethylene glycol, and 1,2-propylene glycol. From the standpoint of reactivity, ethanol, 1-propanol, and 2-propanol are preferred.

The solvent is preferably used in an amount of 1 to 80% by weight, more preferably 5 to 50% by weight of the overall reaction system or liquid. An amount of the solvent in the range keeps the reaction system uniform and allows for efficient progress of reaction.

Although the addition reaction conditions are not particularly limited, the reaction system is preferably heated at a temperature of 50 to 150° C., more preferably 80 to 120° C. for about 1 to 10 hours and kept under reflux.

At the end of addition reaction, the method may include the step of using activated carbon to remove the platinum or rhodium catalyst. An amount of activated carbon used is preferably 0.001 to 5.0% by weight, more preferably 0.01 to 1.0% by weight of the overall reaction system. An amount of activated carbon in the range prevents coloration of the resin.

If necessary, the method may include the step of removing residual hydrosilyl groups. Particularly when the organosilicon resin is used in cosmetic and analogous applications, the step of removing hydrosilyl groups should preferably be included because there is a possibility that hydrosilyl groups deactivate via dehydrogenation reaction with the lapse of time, which is undesirable from the aspect of safety.

The step of removing hydrosilyl groups may include adding a basic catalyst (e.g., alkali metal carbonate, alkali metal hydrogencarbonate or alkali metal hydroxide) for hydrolyzing unreacted hydrosilyl groups therewith, and adding an amount of an acidic catalyst equal to the molar equivalent of the basic catalyst for neutralization. Suitable basic catalysts include strong base catalysts such as lithium hydroxide, sodium hydroxide, potassium hydroxide, calcium hydroxide and barium hydroxide, and weak base catalysts such as sodium carbonate, calcium carbonate and sodium hydrogencarbonate. For promoting dehydrogenation reaction, it is preferred to use a strong base catalyst, typically sodium hydroxide. Suitable acidic catalysts include hydrochloric acid, sulfuric acid, sulfurous acid, fuming sulfuric acid, oxalic acid, p-toluenesulfonic acid, methanesulfonic acid, trifluoroacetic acid, trifluoromethanesulfonic acid, phosphoric acid, formic acid, acetic acid, propionic acid, benzoic acid, and citric acid. Most often, rather than the use of the acid or base alone, the acid or base is preferably used along with water while the system is heated at a temperature below the boiling point of water.

If necessary, the method may include the step of deodorizing the resin at the end of addition reaction. Particularly when the organosilicon resin is used in cosmetic and analogous applications, the deodorizing step should preferably be included because the resin can odorize with the lapse of time. The general odorizing mechanism of polyether-modified silicone is described as follows. When addition reaction is carried out between allyl etherified polyether and hydrogenpolyorganosiloxane in the presence of a platinum catalyst, internal arrangement of the allyl group occurs as side reaction whereby propenyl etherified polyether is formed. Since this propenyl etherified polyether is non-reactive with hydrogenpolyorganosiloxane, it remains in the system as an impurity. When water acts on the propenyl etherified polyether, propenyl ether is hydrolyzed to form propionaldehyde which is a cause of offensive odor. It is known that this hydrolysis reaction is promoted in the presence of an acid catalyst. When polyether-modified silicone is used in an aqueous cosmetic composition, its acidity/basicity nature turns toward acidity with the lapse of time due to oxidative degradation of polyether, whereby the above hydrolysis reaction is promoted, causing to develop offensive odor.

Two formulations are typical of the deodorizing step. The first formulation is by adding an acidic catalyst to the solution after addition reaction, hydrolyzing all the propenyl ether remaining in the system and stripping off the resulting propionaldehyde for purification (see JP 2137062).

Examples of the acidic catalyst used in the first formulation include hydrochloric acid, sulfuric acid, sulfurous acid, fuming sulfuric acid, oxalic acid, p-toluenesulfonic acid, methanesulfonic acid, trifluoroacetic acid, trifluoromethanesulfonic acid, phosphoric acid, formic acid, acetic acid, propionic acid, benzoic acid, and citric acid. The acid is often used in combination with water. When the acid used must be removed later, an acid with a low boiling point such as hydrochloric acid, formic acid, acetic acid or trifluoroacetic acid is preferred. From the standpoint of efficient treatment, a strong acid such as hydrochloric acid or trifluoroacetic acid is preferably used.

The treatment temperature is preferably equal to or lower than 80° C. in order to prevent hydrophilic groups from oxidation. The amount of an acidic aqueous solution added is preferably 0.1 to 100% by weight, more preferably 5 to 30% by weight based on the organic group-modified organosilicon resin.

The procedure preferred from the standpoint of productivity includes adding an acidic aqueous solution to the reaction solution so as to adjust the solution at or below pH7, stirring the solution while heating, and purification by stripping. The strip purification may be performed under atmospheric or reduced pressure, and the temperature is preferably not higher than 120° C. For efficient strip purification at such temperature, stripping is preferably performed under reduced pressure, or if under atmospheric pressure, in a stream of inert gas such as nitrogen or argon.

The second formulation is by adding hydrogen to the solution after addition reaction to convert the unsaturated double bond to alkyl (so-called hydrogenation reaction), for thereby consistently controlling the formation of propionaldehyde with the lapse of time (see U.S. Pat. No. 5,225,509 and JP-A H07-330907).

The hydrogenation reaction may use either hydrogen or metal hydride and be either homogeneous or heterogeneous reaction. These parameters may be selected independently or combined together. Among others, heterogeneous catalytic hydrogenation reaction in the presence of a solid catalyst is most preferred in view of the advantage that the catalyst used is not left in the product.

Suitable solid catalysts include metals alone or compounds thereof such as nickel, palladium, platinum, rhodium, cobalt, chromium, copper and iron. The catalyst may not be carried on a support, but if the support is used, activated carbon, silica, silica alumina, alumina, and zeolite may be suitable as the support. The catalysts may be used alone or in combination. Among others, Raney nickel catalyst is most preferred because of low cost. Since Raney nickel catalyst is generally used after activation with alkali, it is necessary to carefully measure the pH of the reaction solution. Also, since the reaction system becomes weakly alkaline, hydrolytic reaction with an acidic aqueous solution is effective for deodorization.

In general, hydrogenation reaction is preferably carried out at a temperature of 50 to 200° C. and a pressure of 1 to 100 MPa. The reaction may be either batchwise or continuous. In the case of batchwise reaction, the reaction time is generally 3 to 12 hours though it depends on the amount of catalyst, temperature and the like. The hydrogen pressure may be suitably adjusted to a certain pressure. The end of hydrogenation reaction may be judged by carefully monitoring the system pressure by a pressure gauge because the end of hydrogenation reaction is the time when the hydrogen pressure ceases to change.

By such a treatment as acid treatment or hydrogenation reaction, the organic group-modified organosilicon resin may be purified to an aldehyde content of up to 70 ppm, more preferably up to 20 ppm, and even more preferably up to 10 ppm.

The two formulations of deodorizing step may be combined together. The formulation of acid treatment is able to decompose off the aldehyde compound, but limited in complete removal of unsaturated double bond, and thus fails to completely suppress formation of aldehyde which is a cause of odor. On the other hand, the formulation of hydrogenation reaction is able to eliminate the unsaturated double bond and hence, to reduce the amount of aldehyde compound resulting therefrom. However, the aldehyde condensate resulting from condensation of some aldehyde is left within the system even after the above treatment, and is difficult to remove by strip purification. Then complete deodorization is possible by subjecting the solution after addition reaction to hydrogenation reaction for converting the residual unsaturated double bond to alkyl, and then adding an acid catalyst to the system to decompose the aldehyde condensate therein. See WO 2000/05588.

Physical Properties of Organic Group-Modified Organosilicon Resin

The organic group-modified organosilicon resin having the average compositional formula (1) is in solid or liquid form at 25° C. and should preferably have a weight average molecular weight (Mw) of 1,000 to 100,000, with a Mw of 3,000 to 50,000 being more preferred from the standpoints of performance and efficient filtration or operation. It is noted that Mw is measured versus polystyrene standards by gel permeation chromatography (GPC).

When the organic group-modified organosilicon resin has an HLB value of 0.1 to 15 as measured by the Griffin method, it may be emulsified and utilized as an emulsifier for forming W/O or O/W emulsions. Particularly when the resin has an HLB value of 0.1 to 5.5, it may be utilized as an emulsifier for forming W/O emulsions. By the Griffin method, the HLB value is defined as HLB=20×{(total of molecular weights of hydrophilic portions)/(overall molecular weight)}. The HLB value is a numerical value representing the affinity of a surfactant to water and oil.

When the organic group-modified organosilicon resin is used as a W/O type emulsifier, an emulsion having a high water content and a large particle size is obtained as compared with conventional surfactants such as polyether-modified linear organosiloxanes. This emulsion remains relatively stable although the general knowledge suggests that an emulsion having a large particle size tends to coalesce and is unstable. This emulsion may be used to prepare a cosmetic composition of water break type which gives a fresh light feel when applied to the skin.

The organic group-modified organosilicon resin is useful not only as an emulsifier, but also as an additive, for example, for the purposes of improving the dispersibility of powder and assisting adsorption to damaged hair.

Cosmetic Composition

The organic group-modified organosilicon resin may be used in a variety of applications, typically as one ingredient (A) in cosmetic compositions of all types which are externally applied to the skin and hair. The organic group-modified organosilicon resin (A) is preferably used in an amount of 0.1 to 40% by weight based on the overall cosmetic composition. When the organosilicon resin (A) is used as an emulsifier in preparing emulsions, it is more preferably used in an amount of 0.1 to 5% by weight based on the overall cosmetic composition. When the organosilicon resin (A) is used as a dispersant in dispersing powder to form slurries, it is more preferably used in an amount of 0.1 to 15% by weight based on the overall cosmetic composition.

The cosmetic composition of the invention may comprise various other ingredients which are commonly used in cosmetics, for example, (B) oil, (C) powder, (D) surfactant, (E) crosslinked organopolysiloxane, (F) film-forming agent, (G) aqueous ingredient, (H) wax, and (I) other additives. Each of these ingredients may be used alone or in admixture, and some or all these ingredients may be used in combination. Depending on a particular type of cosmetic composition, any suitable ingredients may be selected from these ingredients and the amounts of such ingredients may be determined as appropriate in compliance with their common use.

(B) Oil

The oil may be either solid, semi-solid, or liquid at room temperature. Examples include silicone oils, naturally occurring animal and plant oils and fats, semi-synthetic oils and fats, hydrocarbon oils, higher alcohols, fatty acids, ester oils and fluorinated oils. When used, the amount of oil blended is preferably 1 to 85% by weight, more preferably 15 to 40% by weight based on the overall cosmetic composition, though not limited thereto.

Silicone Oil

The silicone oil used herein may be any of silicone oils which are commonly blended in cosmetics. Examples include linear or branched organopolysiloxanes ranging from low viscosity to high viscosity such as dimethylpolysiloxane, decamethylcyclopentasiloxane, dodecamethylcyclohexasiloxane, disiloxane, trisiloxane, methyltrimethicone, caprylylmethicone, methylphenylpolysiloxane, methylhexylpolysiloxane, methylhydrogenpolysiloxane, dimethylsiloxane-methylphenylsiloxane copolymers; silicone rubbers such as amino-modified organopolysiloxane, pyrrolidone-modified organopolysiloxane, pyrrolidone carboxylic acid-modified organopolysiloxane, gum-like dimethylpolysiloxane having a high degree of polymerization, gum-like amino-modified organopolysiloxane, gum-like dimethylsiloxane-methylphenylsiloxane copolymers; and silicone gum, silicone gum in cyclic organopolysiloxane, trimethylsiloxysilicic acid, trimethylsiloxysilicic acid in cyclic siloxane, higher alkoxy-modified silicone (e.g., stearoxysilicone), higher fatty acid-modified silicone, alkyl-modified silicone, long chain alkyl-modified silicone, amino acid-modified silicone, fluorine-modified silicone, silicone resins and solutions of silicone resins. Of these, preferred are volatile silicones and low-viscosity silicones (e.g., TMF-1.5, KF-995, KF-96A-2cs, and KF-96A-6cs commercially available from Shin-Etsu Chemical Co., Ltd.) giving a fresh feel on use, phenyl silicones (e.g., KF-56A and KF-54HV commercially available from Shin-Etsu Chemical Co., Ltd.) used for the purpose of improving compatibility with other oils or lustering, and silicone wax (e.g., KP-561P, KP-562P, and KF-7020S commercially available from Shin-Etsu Chemical Co., Ltd.) used for the purpose of lustering or adjusting feel on use. These silicone oils may be used alone or in admixture.

(C) Powder

The powder used herein is not particularly limited as long as it is commonly blended in cosmetics. Examples include pigments and silicone spherical powder. When used, the amount of powder blended is preferably 0.1 to 90% by weight, more preferably 1 to 35% by weight based on the overall cosmetic composition, though not limited thereto.

Pigment

The pigment used herein is not particularly limited as long as it is commonly blended in makeup cosmetics. Examples include inorganic pigments such as talc, mica, kaolin, silica, calcium carbonate, zinc oxide, titanium dioxide, red iron oxide, yellow iron oxide, black iron oxide, ultramarine, Prussian blue, carbon black, substoichiometric titanium oxide, cobalt violet, chromium oxide, chromium hydroxide, cobalt titanate, bismuth oxychloride, titanium-mica base pearlescent pigment; organic pigments in the form of zirconium, barium or aluminum lake such as Red #201, Red #202, Red #204, Red #205, Red #220, Red #226, Red #228, Red #405, Orange #203, Yellow #205, Yellow #4, Yellow #5, Blue #1, Blue #404, Green #3; natural dyes such as chlorophyll and β-carotene; and dyes. Powders which are treated with silicones, esters, amino acids and fluorine to be hydrophobic are also included. Examples of hydrophobized inorganic powder include hydrophobized titanium dioxide and hydrophobized iron oxide (e.g., KTP-09W, 09Y, 09R, 09B commercially available from Shin-Etsu Chemical Co., Ltd.), and dispersions of hydrophobized microparticulate titanium dioxide or hydrophobized microparticulate zinc oxide (e.g., SPD-T5, T6, T5L, Z5, Z6, Z5L commercially available from Shin-Etsu Chemical Co., Ltd.).

Silicone Spherical Powder

Suitable silicone spherical powders include crosslinked silicone powders (i.e., so-called silicone rubber powder consisting of organopolysiloxane having crosslinked structure of repeating chains of diorganosiloxane units), and silicone resin particles (particles of polyorganosilsesquioxane resin of three-dimensional network structure). They are known as (dimethicone/vinyldimethicone) cross polymer and polymethylsilsesquioxane. They are commercially available in powder form or swollen form with silicone oil, under the trade name of KMP-598, 590, 591, KSG-016F from Shin-Etsu Chemical Co., Ltd. These powders may be used alone or in admixture.

In particular, silicone resin-coated silicone rubber powders are used in sunscreens, makeups and concealers because of their feel improving effect (e.g., anti-sticky) and morphological correcting effect to wrinkles or pores. Examples of the silicone resin-coated silicone rubber powder include (vinyldimethicone/methiconesilsesquioxane) cross polymer, (diphenyldimethicone/vinyldiphenyldimethicone/silsesquioxane) cross polymer, polysilicone-22, and polysilicone-1 cross polymer, as expressed according to the nomenclature of cosmetic ingredients. They are commercially available under the trade name of KSP-100, 101, 102, 105, 300, 411, 441 from Shin-Etsu Chemical Co., Ltd. These powders may be used alone or in admixture.

(D) Surfactant

The surfactant used herein is not particularly limited as long as it is commonly used in cosmetics. Suitable surfactants include nonionic, anionic, cationic and ampholytic surfactants, which may be used alone or in admixture. Preferred examples of the surfactant include partially crosslinked polyether-modified silicone, partially crosslinked polyglycerol-modified silicone, linear or branched polyoxyethylene-modified organopolysiloxane, linear or branched polyoxyethylenepolyoxypropylene-modified organopolysiloxane, linear or branched polyoxyethylene/alkyl-co-modified organopolysiloxane, linear or branched polyoxyethylenepolyoxypropylene/alkyl-co-modified organopolysiloxane, linear or branched polyglycerol-modified organopolysiloxane, and linear or branched polyglycerollalkyl-co-modified organopolysiloxane. In these surfactants, preferably the content of hydrophilic polyoxyethylene, polyoxyethylenepolyoxypropylene or polyglycerol residues accounts for 10 to 70% of the molecule. They are commercially available under the trade name of KSG-210, 240, 310, 320, 330, 340, 320Z, 350Z, 710, 810, 820, 830, 840, 820Z, 850Z, KF-6011, 6013, 6017, 6043, 6028, 6038, 6048, 6100, 6104, 6105, 6106, KP-578 from Shin-Etsu Chemical Co., Ltd. When used, the amount of the surfactant blended is preferably 0.01 to 15% by weight based on the cosmetic composition.

(E) Crosslinked Organopolysiloxane

The crosslinked organopolysiloxane used herein is not particularly limited as long as it is commonly used in cosmetics. The crosslinked organopolysiloxane may be used alone or in admixture. Unlike the silicone powder (C) and the surfactant (D), the crosslinked organopolysiloxane is an elastomer which is free of a polyether or polyglycerol structure in its molecule, and exhibits structural viscosity when it is swollen with oil. Examples include (dimethicone/vinyldimethicone) cross polymer, (dimethicone/phenylvinyldimethicone) cross polymer, (vinyldimethicone/lauryldimethicone) cross polymer, and (laurylpolydimethylsiloxyethyldimethicone/bisvinyldimethicone) cross polymer. They are commercially available in the form of oil-containing swollen siloxane which is liquid at room temperature, under the trade name of KSG-15, 1510, 16, 1610, 18A, 19, 41A, 42A, 43, 44, 042Z, 045Z, 048Z from Shin-Etsu Chemical Co., Ltd. When used, the amount of the crosslinked organopolysiloxane blended is preferably 0.01 to 30% by weight based on the cosmetic composition.

(F) Film-Forming Agent

The film-forming agent used herein is not particularly limited as long as it is commonly used in cosmetics. Examples include latexes such as polyvinyl alcohol, polyvinyl pyrrolidone, polyvinyl acetate, polyalkyl acrylates; cellulose derivatives such as dextrin, alkyl celluloses, and nitrocellulose; silicone-modified polysaccharides such as pullulan tri(trimethylsiloxy)silylpropylcarbamate, acrylic silicone base graft copolymers such as (alkyl acrylate/dimethicone) copolymers, silicone resins such as trimethylsiloxysilicic acid, silicone base resins such as silicone-modified polynorbomene and fluorine-modified silicone resins, fluoro-resins, aromatic hydrocarbon resins, polymer emulsion resins, terpene resins, polybutene, polyisoprene, alkyd resins, polyvinyl pyrrolidone-modified polymers, rosin-modified resins, and polyurethane.

Among these, silicone base film-forming agents are preferred. More preferred examples include, but are not limited to, pullulan tri(trimethylsiloxy)silylpropylcarbamate (commercially available in solvent solution form as TSPL-30-D5, ID from Shin-Etsu Chemical Co., Ltd.), (alkyl acrylate/dimethicone) copolymers (commercially available in solvent solution form as KP-543, 545, 549, 550, 545L from Shin-Etsu Chemical Co., Ltd.), trimethylsiloxysilicic acid (commercially available in solvent solution form as KF-7312J, X-21-5250 from Shin-Etsu Chemical Co., Ltd.), silicone-modified polynorbomene (commercially available in solvent solution form as NBN-30-ID from Shin-Etsu Chemical Co., Ltd.), and organopolyvinyl alcohol copolymers. The film-forming agent may be used alone or in admixture. When used, the amount of the film-forming agent blended is preferably 0.1 to 20% by weight based on the cosmetic composition.

(G) Aqueous Ingredient

The aqueous ingredient used herein is not particularly limited as long as it is commonly used in cosmetics. Examples include water and humectants, which may be used alone or in admixture. When used, the amount of the aqueous ingredient blended is preferably 0.1 to 90% by weight based on the cosmetic composition.

Water

Examples of water include purified water commonly used in cosmetics, distilled water from fruits and plants, as well as sea water, hot spring water, and peat water as expressed according to the nomenclature of cosmetic ingredients.

Humectant

Suitable humectants include lower alcohols such as ethanol and isopropanol; sucrose alcohols such as sorbitol, maltose and xylitol; polyhydric alcohols such as butylene glycol, dibutylene glycol, propylene glycol, dibutylene glycol, pentylene glycol, decanediol, octanediol, hexanediol, erythritol, glycerol, diglycerol, and polyethylene glycol; glucose, glyceryl glucoxide, betaine, hyaluronic acid, chondroitin sulfate, pyrrolidone carboxylate, polyoxyethylene methyl glucoxide, and polyoxypropylene methyl glucoxide.

(H) Wax

The wax used herein is not particularly limited as long as it is commonly used in cosmetics. Suitable waxes include hydrocarbon waxes such as ceresin, ozokerite, paraffin, synthetic wax, microcrystalline wax, polyethylene wax; plant-derived waxes such as carnauba wax, rice wax, rice bran wax, jojoba wax (inclusive of extremely hydrogenated jojoba wax), candelilla wax; and animal-derived waxes such as whale wax, bee wax and insect wax, which may be used alone or in admixture. When used, the amount of the wax blended is preferably 0.1 to 10% by weight based on the cosmetic composition.

(I) Other Additives

Other additives include oil-soluble gelling agents, antiperspirants, UV absorbers, preservatives, bactericides, perfumes, salts, antioxidants, pH adjusting agents, chelating agents, refreshing agents, anti-inflammatory agents, skin improving agents (brightening agent, cell activating agent, anti-skin-roughening agent, blood flow promotor, skin astringent, antiseborrheic agent), vitamins, amino acids, water-soluble polymers, fibers, and inclusion compounds.

Oil-Soluble Gelling Agent

Suitable oil-soluble gelling agents include metal soaps such as aluminum stearate, magnesium stearate, and zinc myristate; amino acid derivatives such as N-lauroyl-L-glutamic acid and α,γ-di-n-butylamine; dextrin fatty acid esters such as dextrin palmitate, dextrin stearate, and dextrin 2-ethylhexanate palmitate; sucrose fatty acid esters such as sucrose palmitate and sucrose stearate; fructooligosaccharide fatty acid esters such as fructooligosaccharide stearate and fructooligosaccharide 2-ethylhexanoate; benzylidene derivatives of sorbitol such as monobenzylidene sorbitol and dibenzylidene sorbitol; and organo-modified clay minerals such as disteardimonium hectorite, stearalkonium hectorite and hectorite.

UV Absorber

Suitable UV absorbers include homomenthyl salicylate, octocrylene, 4-tert-butyl-4'-methoxydibenzoylmethane, 4-(2-β-glucopyranosiloxy)propoxy-2-hydroxybenzophenone, octyl salicylate, hexyl 2-[4-(diethylamino)-2-hydroxybenzoyl]benzoate, dihydroxydimethoxybenzophenone, sodium dihydroxydimethoxybenzophenonedisulfonate, dihydroxybenzophenone, dimethicodiethylbenzal malonate, 1-(3,4-dimethoxyphenyl)-4,4-dimethyl-1,3-pentanedione, 2-ethylhexyl dimethoxybenzylidenedioxoimidazolidine propionate, tetrahydroxybenzophenone, terephthalylidene dicamphor sulfonic acid, 2,4,6-tris[4-(2-ethylhexyloxycarbonyl)anilino]-1,3,5-triazine, methylbis(trimethylsiloxy)silylisopentyl trimethoxycinnamate, drometrizole trisiloxane, 2-ethylhexyl p-dimethylaminobenzoate, isopropyl p-methoxycinnamate, 2-ethylhexyl p-methoxycinnamate, 2,4-bis[{4-(2-ethylhexyloxy)-2-hydroxy}-phenyl]-6-(4-methoxyphenyl)-1,3,5-triazine, 2-hydroxy-4-methoxybenzophenone, hydroxymethoxybenzophenone sulfonic acid and trihydrate thereof, sodium hydroxymethoxybenzophenone sulfonate, phenylbenzimidazole sulfonic acid, and 2,2'-methylenebis(6-(2H-benzotriazol-2-yl)-4-(1,1,3,3-tetramethylbutyl)phenol).

Also, a UVA absorber (e.g., hexyl diethylaminohydroxybenzoylbenzoate) may be combined with a UVB absorber (e.g., ethylhexyl methoxycinnamate). Any two or more of the foregoing may be used in combination.

Preservative and Bactericide

Examples of the preservative and bactericide include alkyl p-hydroxybenzoates, benzoic acid, sodium benzoate, sorbic acid, potassium sorbate, phenoxyethanol, imidazolidinium urea, salicylic acid, isopropyl methyl phenol, carbolic acid, p-chloro-m-cresol, hexachlorophene, benzalkonium chloride, chlorohexidine chloride, trichlorocarbaniride, iodopropinyl butylcarbamate, polylysine, photosensitizer, silver, and plant extracts.

The cosmetic composition may be of emulsion or non-aqueous form. The emulsion form is selected when a fresh feel on use is desired, and the emulsion may be any of O/W, W/O, O/W/O and W/O/W emulsions. The non-aqueous composition is selected when unctuous texture or water resistance is desired. In either form, a satisfactory cosmetic composition is obtained. As used herein, the term "non-aqueous composition" refers to a composition substantially free of water. In the case of W/O emulsion, a weight ratio of the content of water phase to the total content of water and oil phases is preferably at least 0.6/1, more preferably at least 0.7/1, and most preferably at least 0.75/1.

The type of the cosmetic composition is not particularly limited as long as it contains essential ingredients. For example, the cosmetic composition may be implemented as toilet water, lotion, milky lotion, cream, hair care, foundation, foundation primer, sunscreen, concealer, cheek color, lipstick, lip care, gloss, balm, mascara, eyeshadow, eyeliner, body makeup, deodorant, nail treatment, etc. The cosmetic composition may take a variety of formulas including liquid, cream, solid, paste, gel, moose, souffle, clay, powder, stick, etc.

EXAMPLE

Preparation Examples, Examples, and Comparative Examples are shown below for further illustrating the invention although the invention is not limited thereto. All percent (%) are by weight unless otherwise stated. Exemplary organic group-modified organosilicon resins are shown in Preparation Examples, whereas exemplary cosmetic compositions shown in Examples and Comparative Examples. Me stands for methyl, and Mw is weight average molecular weight.

Preparation Example 1

Preparation of Organic Group-Modified Organosilicon Resin

A reactor was charged with 1,000 g of a 50% decamethylcyclopentasiloxane solution of powdered hydrosilyl-containing organosilicon resin having the average compositional formula (E1) (Mw 5,500, hydrogen gas release 65.1 mL/g), 205 g of organopolysiloxane having the formula (E2), 1,000 g of 2-propanol, and 1.3 g of a 0.5% 2-propanol solution of chloroplatinic acid and heated at 80° C. for 6 hours for reaction. Thereafter, 577 g of polyoxyalkylene having the formula (E3) was added to the reactor, which was heated at 80° C. for 6 hours to continue reaction. The reactor was heated under reduced pressure to distill off the solvent.

Then 250 g of ethanol was added, 5 g of 5% sodium hydroxide aqueous solution was added for thereby hydrolyzing unreacted hydrosilyl groups, and 0.63 g of conc. hydrochloric acid was added for neutralization. After the neutralization, 150 g of 0.01N hydrochloric acid aqueous solution was added for thereby hydrolyzing allyl ether groups of unreacted polyoxyalkylene, and the reaction solution was neutralized with 2.6 g of 5% sodium bicarbonate aqueous solution. The reaction solution was heated under reduced pressure to distill off the solvent and filtered, obtaining a decamethylcyclopentasiloxane solution of organic group-modified organosilicon resin having the average compositional formula (E4). The decamethylcyclopentasiloxane solution of organic group-modified organosilicon resin was heated at 120-130° C. under reduced pressure to remove decamethylcyclopentasiloxane, yielding the organic group-modified organosilicon resin in colorless transparent liquid form. The product (resin) had an HLB value of 9.0.

$(Me_3SiO_{1/2})_{22.7}(HMe_2SiO_{1/2})_{16.1}(SiO_2)_{43.9}$    Average compositional formula (E1):

$CH_2=CH-(SiO(CH_3)_2)_8-Si(CH_3)_3$    Formula (E2):

$CH_2=CH-CH_2-O-(C_2H_4O)_{10}-CH_3$    Formula (E3):

$(Me_3SiO_{1/2})_{22.7}(R^2Me_2SiO_{1/2})_{3.2}(R^3Me_2SiO_{1/2})_{12.8}(SiO_{4/2})_{43.5}$    Average compositional formula (E4):

$R^2=-CH_2-CH_2-CH_2-O-(C_2H_4O)_{10}-CH_3$ $R^3=-CH_2-CH_2-(SiO(CH_3)_2)_8-Si(CH_3)_3$ (Me is methyl, herein after.)

Preparation Example 2

Preparation of Organic Group-Modified Organosilicon Resin, Polymer I

A reactor was charged with 1,300 g of a 50% decamethylcyclopentasiloxane solution of powdered hydrosilyl-containing organosilicon resin having the average compositional formula (E5) (Mw 7,980, hydrogen gas release 52.4 mL/g), 716 g of organopolysiloxane having the formula (E6), 1,300 g of 2-propanol, and 1.7 g of a 0.5% 2-propanol solution of chloroplatinic acid and heated at 100° C. for 6 hours for reaction. Thereafter, 62 g of polyoxyalkylene having the formula (E7) was added to the reactor, which was heated at 100° C. for 6 hours to continue reaction. The reactor was heated under reduced pressure to distill off the solvent. Then 325 g of ethanol was added, 6.5 g of 5% sodium hydroxide aqueous solution was added for thereby hydrolyzing unreacted hydrosilyl groups, and 0.8 g of conc. hydrochloric acid was added for neutralization. After the neutralization, 195 g of 0.01N hydrochloric acid aqueous solution was added for thereby hydrolyzing allyl ether groups of unreacted polyoxyalkylene, and the reaction solution was neutralized with 3.3 g of 5% sodium bicarbonate aqueous solution. The reaction solution was heated under reduced pressure to distill off the solvent and filtered, obtaining a decamethylcyclopentasiloxane solution of organic group-modified organosilicon resin having the average compositional formula (E8). The decamethylcyclopentasiloxane solution of organic group-modified organosilicon resin was heated at 120-130° C. under reduced pressure to remove decamethylcyclopentasiloxane, yielding the organic group-modified organosilicon resin in colorless transparent liquid form. The product (resin) had an HLB value of 1.0.

$(Me_3SiO_{1/2})_{32.9}(HMe_2SiO_{1/2})_{17.5}(Me_2SiO)_{2.4}(SiO_2)_{66.1}$    Average compositional formula (E5):

$CH_2=CH-(SiO(CH_3)_2)_6-Si(CH_3)_3$    Formula (E6):

$CH_2=CH-CH_2-O-(C_2H_4O)_9-H$    Formula (E7):

$(Me_3SiO_{1/2})_{32.9}(R^2Me_2SiO_{1/2})_{1.8}(R^3Me_2SiO_{1/2})_{15.7}(Me_2SiO_{2/2})_{2.4}(SiO_{4/2})_{66.1}$    Average compositional formula (E8):

$R^2=-CH_2-CH_2-CH_2-O-(C_2H_4O)_9-H$ $R^3=-CH_2-CH_2-(SiO(CH_3)_2)_6-Si(CH_3)_3$

Preparation Example 3

Preparation of Organic Group-Modified Organosilicon Resin

A reactor was charged with 800 g of a 50% decamethylcyclopentasiloxane solution of powdered hydrosilyl-containing organosilicon resin having the average compositional formula (E9) (Mw 16,200, hydrogen gas release 76.5 mL/g), 184 g of organopolysiloxane having the formula (E10), 800 g of ethanol, and 1.2 g of a 0.5% 2-propanol solution of chloroplatinic acid and heated at 80° C. for 6 hours for reaction. Thereafter, 587 g of polyoxyalkylene having the formula (E11) was added to the reactor, which was heated at 100° C. for 6 hours to continue reaction. The reactor was heated under reduced pressure to distill off the solvent. Then 200 g of ethanol was added, 4.0 g of 5% sodium hydroxide aqueous solution was added for thereby hydrolyzing unreacted hydrosilyl groups, and 0.5 g of conc. hydrochloric acid was added for neutralization. After the neutralization, 120 g of 0.01N hydrochloric acid aqueous solution was added for thereby hydrolyzing allyl ether groups of unreacted polyoxyalkylene, and the reaction solution was neutralized with 2.0 g of 5% sodium bicarbonate aqueous solution. The reaction solution was heated under reduced pressure to distill off the solvent and filtered, obtaining a decamethylcyclopentasiloxane solution of organic group-modified organosilicon resin having the average compositional formula (E12). The decamethylcyclopentasiloxane solution of organic group-modified organosilicon resin was heated at 120-130° C. under reduced pressure to remove decamethylcyclopentasiloxane, yielding the organic group-modified organosilicon resin in colorless transparent liquid form. The product (resin) had an HLB value of 10.0.

$(Me_3SiO_{1/2})_{51.9}(HMe_2SiO_{1/2})_{55.3}(SiO_2)_{138.2}$    Average compositional formula (E9):

$CH_2=CH-Si(OSi(CH_3)_3)_3$    Formula (E10):

$CH_2=CH-CH_2-O-(C_2H_4O)_{15}-CH_3$    Formula (E11):

$(Me_3SiO_{1/2})_{51.9}(R^2Me_2SiO_{1/2})_{33.2}(R^3Me_2SiO_{1/2})_{22.1}(SiO_{4/2})_{138.2}$    Average compositional formula (E12):

$R^2=-CH_2-CH_2-CH_2-O-(C_2H_4O)_{15}-CH_3$ $R^3=-CH_2-CH_2-Si(OSi(CH_3)_3)_3$

Preparation Example 4

Preparation of Organic Group-Modified Organosilicon Resin, Polymer II

A reactor was charged with 900 g of a 50% decamethylcyclopentasiloxane solution of powdered hydrosilyl-containing organosilicon resin having the average compositional formula (E13) (Mw 5,350, hydrogen gas release 57.0 mL/g), 575 g of organopolysiloxane having the formula (E14), 900 g of 2-propanol, and 1.1 g of a 0.5% 2-propanol solution of chloroplatinic acid and heated at 95° C. for 6 hours for reaction. Thereafter, 50.1 g of polyoxyalkylene having the formula (E15) was added to the reactor, which was heated at 100° C. for 6 hours to continue reaction. The reactor was heated under reduced pressure to distill off the solvent. Then 225 g of ethanol was added, 4.5 g of 5% sodium hydroxide aqueous solution was added for thereby hydrolyzing unreacted hydrosilyl groups, and 0.6 g of conc. hydrochloric acid was added for neutralization. After the neutralization, 135 g of 0.01N hydrochloric acid aqueous solution was added for thereby hydrolyzing allyl ether groups of unreacted polyoxyalkylene, and the reaction solution was neutralized with 2.3 g of 5% sodium bicarbonate aqueous solution. The reaction solution was transferred to an autoclave where 50 g of Raney nickel was added and reaction was run at 100° C. for 3 hours in a hydrogen stream under a hydrogen pressure of 1 MPa. The reaction solution was heated under reduced pressure to distill off the solvent and filtered, obtaining a decamethylcyclopentasiloxane solution of organic group-modified organosilicon resin having the average compositional formula (E16). The decamethylcyclopentasiloxane solution of organic group-modified organosilicon resin was heated at 120-130° C. under reduced pressure to remove decamethylcyclopentasiloxane, yielding the organic group-modified organosilicon resin in colorless transparent liquid form. The product (resin) had an HLB value of 1.0.

$(Me_3SiO_{1/2})_{21.9}(HMe_2SiO_{1/2})_{13.6}(SiO_2)_{44.4}$  Average compositional formula (E13):

$CH_2=CH-(SiO(CH_3)_2)_6-Si(CH_3)_3$  Formula (E14):

$CH_2=CH-CH_2-O-(C_2H_4O)_9-H$  Formula (E15):

$(Me_3SiO_{1/2})_{21.9}(R^2Me_2SiO_{1/2})_{1.4}(R^3Me_2SiO_{1/2})_{12.2}(SiO_{1/2})_{44.4}$  Average compositional formula (E16):

$R^2=-CH_2-CH_2-CH_2-O-(C_2H_4O)_9-CH_3$ $R^3=-CH_2-CH_2-(SiO(CH_3)_2)_6-Si(CH_3)_3$

Preparation Example 5

Preparation of 60% Decamethylcyclopentasiloxane Solution of Organic Group-Modified Organosilicon Resin A reactor was charged with 1,100 g of a 50% decamethylcyclopentasiloxane solution of solid hydrosilyl-containing organosilicon resin having the average compositional formula (E17) (Mw 1,600, hydrogen gas release 43.0 mL/g), 235 g of organopolysiloxane having the formula (E18), 1,100 g of 2-propanol, and 1.2 g of a 0.5% 2-propanol solution of chloroplatinic acid and heated at 85° C. for 6 hours for reaction. Thereafter, 403 g of polyoxyalkylene having the formula (E19) was added to the reactor, which was heated at 85° C. for 6 hours to continue reaction. The reactor was heated under reduced pressure to distill off the solvent. Then 275 g of ethanol was added, 5.5 g of 5% sodium hydroxide aqueous solution was added for thereby hydrolyzing unreacted hydrosilyl groups, and 0.7 g of conc. hydrochloric acid was added for neutralization. After the neutralization, 165 g of 0.01N hydrochloric acid aqueous solution was added for thereby hydrolyzing allyl ether groups of unreacted polyoxyalkylene, and the reaction solution was neutralized with 2.8 g of 5% sodium bicarbonate aqueous solution. The reaction solution was heated under reduced pressure to distill off the solvent, filtered, and diluted with decamethylcyclopentasiloxane to a resin concentration of 60%, obtaining a 60% decamethylcyclopentasiloxane solution of organic group-modified organosilicon resin having the average compositional formula (E20).

The decamethylcyclopentasiloxane solution of organic group-modified organosilicon resin was heated at 120-130° C. under reduced pressure to remove decamethylcyclopentasiloxane, obtaining the product in solid powder form. The product had an HLB value of 6.8.

$(Me_3SiO_{1/2})_{7.7}(HMe_2SiO_{1/2})_{3.0}(SiO_2)_{12.9}$  Average compositional formula (E17):

$CH_2=CH-(SiO(CH_3)_2)_6-Si(CH_3)_3$  Formula (E18):

$CH_2=CH-CH_2-O-(C_3H_6O)_{10}-CH_3$  Formula (E19):

$(Me_3SiO_{1/2})_{7.7}(R^2Me_2SiO_{1/2})_{1.8}(R^3Me_2SiO_{1/2})_{1.2}(SiO_{4/2})_{12.9}$  Average compositional formula (E20):

$R^2=-CH_2-CH_2-CH_2-O-(C_3H_6O)_{10}-CH_3$ $R^3=-CH_2-CH_2-(SiO(CH_3)_2)_6-Si(CH_3)_3$

Preparation Example 6

Preparation of Organic Group-Modified Organosilicon Resin

A reactor was charged with 800 g of a 50% octamethylcyclotetrasiloxane solution of powdered hydrosilyl-containing organosilicon resin having the average compositional formula (E21) (Mw 6,400, hydrogen gas release 18.9 mL/g), 72 g of organopolysiloxane having the formula (E22), 800 g of 2-propanol, and 0.6 g of a 0.5% 2-propanol solution of chloroplatinic acid and heated at 105° C. for 6 hours for reaction. Thereafter, 149 g of polyoxyalkylene having the formula (E23) was added to the reactor, which was heated at 105° C. for 6 hours to continue reaction. The reactor was heated under reduced pressure to distill off the solvent. Then 200 g of ethanol was added, 4.0 g of 5% sodium hydroxide aqueous solution was added for thereby hydrolyzing unreacted hydrosilyl groups, and 0.5 g of conc. hydrochloric acid was added for neutralization. After the neutralization, 120 g of 0.01N hydrochloric acid aqueous solution was added for thereby hydrolyzing allyl ether groups of unreacted polyoxyalkylene, and the reaction solution was neutralized with 2.0 g of 5% sodium bicarbonate aqueous solution. The reaction solution was heated under reduced pressure to distill off the solvent and filtered, obtaining a octamethylcyclotetrasiloxane solution of organic group-modified organosilicon resin having the average compositional formula (E24). The octamethylcyclotetrasiloxane solution of organic group-modified organosilicon resin was heated at 120-130° C. under reduced pressure to remove octamethylcyclotetrasiloxane, yielding the organic group-modified organosilicon resin in colorless transparent liquid form. The product (resin) had an HLB value of 4.8.

$(Me_3SiO_{1/2})_{29.2}(HMe_2SiO_{1/2})_{5.4}(MeSiO_{3/2})_{16.2}(SiO_2)_{43.2}$  Average compositional formula (E21):

$CH_2=CH-(SiO(CH_3)_2)_{10}-Si(CH_3)_3$  Formula (E22):

$CH_2=CH-CH_2-O-(C_2H_4O)_{12}-H$  Formula (E23):

$(Me_3SiO_{1/2})_{29.2}(R^2Me_2SiO_{1/2})_{4.0}(R^3Me_2SiO_{1/2})_{1.3}(MeSiO_{3/2})_{16.2}(SiO_{4/2})_{43.2}$  Average compositional formula (E24):

$R^2=-CH_2-CH_2-CH_2-O-(C_2H_4O)_2-CH_3$ $R^3=-CH_2-CH_2-(SiO(CH_3)_2)_{10}-Si(CH_3)_3$

Preparation Example 7

Preparation of Organic Group-Modified Organosilicon Resin

A reactor was charged with 500 g of a 50% decamethylcyclopentasiloxane solution of powdered hydrosilyl-containing organosilicon resin having the average compositional formula (E25) (Mw 10,800, hydrogen gas release 39.8 mL/g), 59.8 g of organopolysiloxane having the formula (E26), 1,000 g of ethanol, and 1.1 g of a 0.5% 2-propanol solution of chloroplatinic acid and heated at 80° C. for 6 hours for reaction. Thereafter, 559 g of polyoxyalkylene having the formula (E27) was added to the reactor, which was heated at 80° C. for 6 hours to continue reaction. The reactor was heated under reduced pressure to distill off the solvent. Then 250 g of ethanol was added, 5.0 g of 5% sodium hydroxide aqueous solution was added for thereby hydrolyzing unreacted hydrosilyl groups, and 0.6 g of conc. hydrochloric acid was added for neutralization. After the neutralization, 150 g of 0.01N hydrochloric acid aqueous solution was added for thereby hydrolyzing allyl ether groups of unreacted polyoxyalkylene, and the reaction solution was neutralized with 2.6 g of 5% sodium bicarbonate aqueous solution. The reaction solution was transferred to an autoclave where 50 g of Raney nickel was added and reaction was run at 100° C. for 3 hours in a hydrogen stream under a hydrogen pressure of 1 MPa. The reaction solution was heated under reduced pressure to distill off the solvent and filtered, obtaining a decamethylcyclopentasiloxane solution of organic group-modified organosilicon resin having the average compositional formula (E28). The decamethylcyclopentasiloxane solution of organic group-modified organosilicon resin was heated at 120-130° C. under reduced pressure to remove decamethylcyclopentasiloxane, yielding the organic group-modified organosilicon resin in colorless transparent liquid form. The product (resin) had an HLB value of 10.0.

$(Me_3SiO_{1/2})_{35.1}(HMe_2SiO_{1/2})_{19.2}(Me_2SiO)_{29.2}$
$(SiO_2)_{75.2}$ Average compositional formula (E25):

$CH_2=CH-(SiO(CH_3)_2)_3-Si(CH_3)_3$ Formula (E26):

$CH_2=CH-CH_2-O-(C_2H_4O)_{10}(C_3H_6O)_5-H$ Formula (E27):

$(Me_3SiO_{1/2})_{35.1}(R^2Me_2SiO_{1/2})_{15.4}(R^3Me_2SiO_{1/2})_{3.8}$
$(Me_2SiO)_{29.2}$
$(SiO_{4/2})_{75.2}$ Average compositional formula (E28):

$R^2=-CH_2-CH_2-CH_2-O-(C_2H_4O)_{10}(C_3H_6O)_5-CH_3$ $R^3=-CH_2-CH_2-(SiO(CH_3)_2)_3-Si(CH_3)_3$

Preparation Example 8

Preparation of 60% Isododecane Solution of Organic Group-Modified Organosilicon Resin A reactor was charged with 1,600 g of a 50% isododecane solution of powdered hydrosilyl-containing organosilicon resin having the average compositional formula (E29) (Mw 8,600, hydrogen gas release 10.5 mL/g), 72.4 g of organopolysiloxane having the formula (E30), 1,600 g of 2-propanol, and 1.0 g of a 0.5% 2-propanol solution of chloroplatinic acid and heated at 90° C. for 6 hours for reaction. Thereafter, 111 g of polyoxyalkylene having the formula (E31) was added to the reactor, which was heated at 90° C. for 6 hours to continue reaction. The reactor was heated under reduced pressure to distill off the solvent. Then 400 g of ethanol was added, 8.0 g of 5% sodium hydroxide aqueous solution was added for thereby hydrolyzing unreacted hydrosilyl groups, and 1.0 g of conc. hydrochloric acid was added for neutralization. After the neutralization, 240 g of 0.01N hydrochloric acid aqueous solution was added for thereby hydrolyzing allyl ether groups of unreacted polyoxyalkylene, and the reaction solution was neutralized with 4.1 g of 5% sodium bicarbonate aqueous solution. The reaction solution was transferred to an autoclave where 50 g of Raney nickel was added and reaction was run at 100° C. for 3 hours in a hydrogen stream under a hydrogen pressure of 1 MPa. The reaction solution was heated under reduced pressure to distill off the solvent, filtered, and diluted with isododecane to a resin concentration of 60%, obtaining a 60% isododecane solution of organic group-modified organosilicon resin having the average compositional formula (E32).

The isododecane solution of organic group-modified organosilicon resin was heated at 120-130° C. under reduced pressure to remove isododecane, obtaining the product in solid powder form. The product had an HLB value of 2.3.

$(Me_3SiO_{1/2})_{52.2}(HMe_2SiO_{1/2})_{4.0}(SiO_2)_{68.3}$ Average compositional formula (E29):

$CH_2=CH-(SiO(CH_3)_2)_5-Si(CH_3)_3$ Formula (E30):

$CH_2=CH-CH_2-O-(C_2H_4O)_{10}-CH_3$ Formula (E31):

$(Me_3SiO_{1/2})_{52.2}(R^2Me_2SiO_{1/2})_{2.4}(R^3Me_2SiO_{1/2})_{1.6}$
$(SiO_{4/2})_{6.3}$ Average compositional formula (E32):

$R^2=-CH_2-CH_2-CH_2-O-(C_2H_4O)_{10}-CH_3$ $R^3=-CH_2-CH_2-(SiO(CH_3)_2)_5-Si(CH_3)_3$

Preparation Example 9

Preparation of Organic Group-Modified Organosilicon Resin

A reactor was charged with 1,300 g of a 50% decamethylcyclopentasiloxane solution of powdered hydrosilyl-containing organosilicon resin having the average compositional formula (E33) (Mw 5,800, hydrogen gas release 25.0 mL/g), 48.8 g of organopolysiloxane having the formula (E34), 1,300 g of ethanol, and 1.2 g of a 0.5% 2-propanol solution of chloroplatinic acid and heated at 90° C. for 6 hours for reaction. Thereafter, 799 g of polyoxyalkylene having the formula (E35) was added to the reactor, which was heated at 90° C. for 6 hours to continue reaction. The reactor was heated under reduced pressure to distill off the solvent. Then 325 g of ethanol was added, 6.5 g of 5% sodium hydroxide aqueous solution was added for thereby hydrolyzing unreacted hydrosilyl groups, and 0.8 g of conc. hydrochloric acid was added for neutralization. After the neutralization, 195 g of 0.01N hydrochloric acid aqueous solution was added for thereby hydrolyzing allyl ether groups of unreacted polyoxyalkylene, and the reaction solution was neutralized with 3.3 g of 5% sodium bicarbonate aqueous solution. The reaction solution was heated under reduced pressure to distill off the solvent and filtered, obtaining a decamethylcyclopentasiloxane solution of organic group-modified organosilicon resin having the average compositional formula (E36). The decamethylcyclopentasiloxane solution of organic group-modified organosilicon resin was heated at 120-130° C. under reduced pressure to remove decamethylcyclopentasiloxane, yielding the organic group-modified organosilicon resin in colorless transparent liquid form. The product (resin) had an HLB value of 10.7.

$(Me_3SiO_{1/2})_{31.1}(HMe_2SiO_{1/2})_{6.5}(SiO_2)_{47.5}$  Average compositional formula (E33):

$CH_2=CH—(SiO(CH_3)_2)_3—Si(CH_3)_3$  Formula (E34):

$CH_2=CH—CH_2—O—(C_2H_4O)_{30}—CH_3$  Formula (E35):

$(Me_3SiO_{1/2})_{31.1}(R^2Me_2SiO_{1/2})_{5.2}(R^3Me_2SiO_{1/2})_{1.3}(SiO_{4/2})_{47.5}$  Average compositional formula (E36):

$R^2=—CH_2—CH_2—CH_2—O—(C_2H_4O)_{30}—CH_3$ $R^3=—CH_2—CH_2—(SiO(CH_3)_2)_3—Si(CH_3)_3$

Preparation Example 10

Preparation of Organic Group-Modified Organosilicon Resin

A reactor was charged with 1,000 g of a 50% decamethylcyclopentasiloxane solution of powdered hydrosilyl-containing organosilicon resin having the average compositional formula (E37) (Mw 7,600, hydrogen gas release 39.7 mL/g), 518 g of organopolysiloxane having the formula (E38), 1,000 g of 2-propanol, and 1.0 g of a 0.5% 2-propanol solution of chloroplatinic acid and heated at 80° C. for 6 hours for reaction. The reactor was heated under reduced pressure to distill off the solvent. Then 250 g of ethanol was added, 5.0 g of 5% sodium hydroxide aqueous solution was added for thereby hydrolyzing unreacted hydrosilyl groups, and 0.6 g of conc. hydrochloric acid was added for neutralization. After the neutralization, 150 g of 0.01N hydrochloric acid aqueous solution was added for thereby hydrolyzing allyl ether groups of unreacted polyoxyalkylene, and the reaction solution was neutralized with 2.6 g of 5% sodium bicarbonate aqueous solution. The reaction solution was heated under reduced pressure to distill off the solvent and filtered, obtaining a 60% decamethylcyclopentasiloxane solution of organic group-modified organosilicon resin having the average compositional formula (E39). The decamethylcyclopentasiloxane solution of organic group-modified organosilicon resin was heated at 120-130° C. under reduced pressure to remove decamethylcyclopentasiloxane, yielding the organic group-modified organosilicon resin in colorless transparent liquid form. The product (resin) had an HLB value of 10.2.

$(Me_3SiO_{1/2})_{38.8}(HMe_2SiO_{1/2})_{13.5}(SiO_2)_{59.3}$  Average compositional formula (E37):

$CH_2=CH—CH_2—O—(C_2H_4O)_{12}—CH_3$  Formula (E38):

$(Me_3SiO_{1/2})_{38.8}(R^2Me_2SiO_{1/2})_{13.5}(SiO_{4/2})_{59.3}$  Average compositional formula (E39):

$R^2=—CH_2—CH_2—CH_2—O—(C_2H_4O)_{12}—CH_3$

The organic group-modified organosilicon resins thus obtained were evaluated for solubility in decamethylcyclopentasiloxane (D5) and emulsification. D5 solubility was evaluated by combining 50% of ingredient and 50% of D5 and observing whether or not the ingredient was dissolved. Emulsification was evaluated by combining 78% of water with an oil phase of 2% of ingredient and 20% of D5 and observing whether or not the mixture was emulsified. Also the form of 100% ingredient at 25° C. was observed.

The results are shown in Table 1.

TABLE 1

| Ingredient | D5 solubility | Emulsification | Form |
|---|---|---|---|
| Trimethylsiloxysilicic acid *1 | dissolved | nil | solid |
| Preparation Example 1 | nil | emulsified | liquid |
| Preparation Example 2 | dissolved | emulsified | liquid |
| Preparation Example 3 | nil | emulsified | liquid |
| Preparation Example 4 | dissolved | emulsified | liquid |
| Preparation Example 5 | nil | emulsified | solid |
| Preparation Example 6 | dissolved | emulsified | liquid |
| Preparation Example 7 | nil | emulsified | liquid |
| Preparation Example 8 | dissolved | emulsified | solid |
| Preparation Example 9 | nil | emulsified | liquid |
| Preparation Example 10 | nil | emulsified | liquid |

*1 trimethylsiloxysilicic acid solution: KF-7312J of Shin-Etsu Chemical Co., Ltd.

Preparation Example 11

Preparation of 60% Solution of Polymer I in Decamethylcyclopentasiloxane (D5)

A nitrogen-purged separable flask was charged with Polymer I and D5, which were stirred at 80° C. with a glass stirrer until uniform dissolution, obtaining 60% solution.

Preparation Example 12

Preparation of 60% Solution of Polymer I in Dimethicone (6cs)

A nitrogen-purged separable flask was charged with Polymer I and dimethicone (6cs), which were stirred at 80° C. with a glass stirrer until uniform dissolution, obtaining 60% solution.

Preparation Example 13

Preparation of 80% Solution of Polymer II in D5

A nitrogen-purged separable flask was charged with Polymer II and D5, which were stirred at 80° C. with a glass stirrer until uniform dissolution, obtaining 80% solution.

Preparation Example 14

Preparation of 80% Solution of Polymer II in Isododecane

A nitrogen-purged separable flask was charged with Polymer II and isododecane, which were stirred at 80° C. with a glass stirrer until uniform dissolution, obtaining 80% solution.

Notably, the polymers can be dissolved not only in D5, dimethicone (6cs) and isododecane, but also in volatile solvents for cosmetic use such as dimethicone (2cs) and methyltrimethicone, and nonvolatile solvents such as triethylhexanoin and isotridecyl isononanoate. The viscosity of the resulting solution can be changed in terms of the composition and molecular weight of the polymer.

(1) Evaluation of Properties

The cosmetic composition (sample) of Example 1 or Comparative Example 1 shown below was evaluated for feel-on-use (or nonsticky feel), lightness (or freshness), and age stability (after 50° C./1 month storage). Ten panel members tested the composition and assigned a point in accordance with the point table of Table 2, from which an average was calculated. The sample was rated according to the following judgment criteria. The results are shown in Tables 3 and 4.

TABLE 2

| Point | Feel-on-use | Lightness | Age stability |
|---|---|---|---|
| 5 | good | good | good |
| 4 | rather good | rather good | rather good |
| 3 | ordinary | ordinary | ordinary |
| 2 | rather bad | rather bad | rather bad |
| 1 | bad | bad | bad |

Points of evaluation

Judgment criteria

⊚: average point ≥4.5
O: 3.5≤average point <4.5
Δ: 2.5≤average point <3.5
X: 1.5≤average point <2.5
XX: average point <1.5

Example 1 and Comparative Example 1

A cosmetic composition was prepared in accordance with the formulation shown in Table 3 and evaluated.

TABLE 3

| | Formulation (%) | Example 1 | Comparative Example 1 |
|---|---|---|---|
| (1) | 60% D5 solution of Polymer I | 2 | — |
| | Polyether-modified silicone *1 | — | 1.2 |
| | Decamethylcyclopentasiloxane (D5) | — | 0.8 |
| | Dimethylpolysiloxane (6cs) | 23 | 23 |
| (2) | Butylene glycol | 5 | 5 |
| | Sodium chloride | 0.5 | 0.5 |
| | Preservative | proper | proper |
| | Purified water | balance | balance |
| Total | | 100 | 100 |
| Evaluation | Feel-on-use | ⊚ | Δ |
| | Lightness | ⊚ | Δ |
| | Age stability | ⊚ | XX |

*1 Polyether-modified silicone: KF-6017 by Shin-Etsu Chemical Co., Ltd.

It is noted that the formulating amount is the amount of the described ingredient (the same holds true, hereinafter).

The cosmetic composition was prepared by step A of mixing ingredients in part (1) until uniform, step B of mixing ingredients in part (2) until uniform, and step C of adding B to A and emulsifying to form W/O emulsion.

As seen from Table 3, the W/O emulsion of Example 1 was good in feel-on-use (or nonsticky feel), lightness (or freshness), and age stability (after 50° C./1 month storage).

Example 2 and Comparative Example 2

A cosmetic composition was prepared in accordance with the formulation shown in Table 4 and evaluated.

TABLE 4

| | Formulation (%) | Example 2 | Comparative Example 2 |
|---|---|---|---|
| (1) | 60% D5 solution of Polymer I | 3 | — |
| | Partially crosslinked dimethylpolysiloxane compound *1 | 1 | 1 |
| | Silicone branched polyether-modified silicone *2 | 0.2 | 2 |
| | Decamethylcyclopentasiloxane (D5) | — | 1.2 |
| | Dimethylpolysiloxane (6cs) | 10.8 | 10.8 |
| (2) | Butylene glycol | 8 | 8 |
| | Ethanol | 5 | 5 |
| | Sodium citrate | 0.2 | 0.2 |
| | Sodium chloride | 0.5 | 0.5 |
| | Purified water | balance | balance |
| Total | | 100 | 100 |
| Evaluation | Feel-on-use | ⊚ | Δ |
| | Lightness | ⊚ | X |
| | Age stability | ⊚ | Δ |

*1 Partially crosslinked dimethylpolysiloxane compound: KSG-15 (crosslink 4-10%, D5 90-96%) by Shin-Etsu Chemical Co., Ltd.
*2 Silicone branched polyether-modified silicone: KF-6028 by Shin-Etsu Chemical Co., Ltd.

The cosmetic composition was prepared by step A of mixing ingredients in part (1) until uniform, step B of mixing ingredients in part (2) until uniform, and step C of adding B to A and emulsifying to form W/O cream.

As seen from Table 4, the W/O cream of Example 2 was good in feel-on-use (or nonsticky feel), lightness (or freshness), and age stability (after 50° C./1 month storage). It has been demonstrated that a cosmetic composition of water break type is readily prepared.

Example 3

W/O Sunscreen Cream

A cosmetic composition was prepared by step A of dispersing ingredients 7 to 9 on a roll mill, step B of mixing ingredients 1 to 6 until uniform, step C of mixing ingredients 10 to 15 until uniform, and step D of adding C to B, emulsifying, adding A to the emulsion to form W/O sunscreen cream.

| | Ingredients | Amount (%) |
|---|---|---|
| 1. | Partially crosslinked polyether-modified silicone compound *1 | 3 |
| 2. | Partially crosslinked dimethylpolysiloxane compound *2 | 10 |
| 3. | Silicone branched polyether-modified silicone *3 | 2.8 |
| 4. | Disteardimonium hectorite | 0.8 |
| 5. | Decamethylcyclopentasiloxane | 16 |
| 6. | Dimethylpolysiloxane (6cs) | 7 |
| 7. | 80% D5 solution of Polymer II | 2.5 |
| 8. | Decamethylcyclopentasiloxane | 9.5 |
| 9. | Metal soap-treated microparticulate titanium oxide | 8 |
| 10. | Dipropylene glycol | 5 |
| 11. | Sodium citrate | 0.2 |
| 12. | Sodium chloride | 0.5 |
| 13. | Ethylhexylglycerin | 0.05 |
| 14. | Dipotassium Glycyrrhizate | 0.05 |
| 15. | Purified water | balance |
| | | 100 |

*1 Partially crosslinked polyether-modified silicone compound: KSG-210 (crosslink 20-30%, dimethylpolysiloxane (6c5) 70-80%) by Shin-Etsu Chemical Co., Ltd.
*2 Partially crosslinked dimethylpolysiloxane compound: KSG-15 (crosslink 4-10%, D5 90-96%) by Shin-Etsu Chemical Co., Ltd.
*3 Silicone branched polyether-modified silicone: KF-6028 by Shin-Etsu Chemical Co., Ltd.

The W/O sunscreen cream delivered light spreading without squeaking, and light feel-on-use without powdery texture. When the organic group-modified organosilicon resin is used as a powder dispersant, it is possible to reduce the viscosity of a slurry and to prepare a low viscosity emulsion.

Example 4

W/O Sunscreen Milk

A cosmetic composition was prepared by step A of mixing ingredients 1 to 10 until uniform, step B of mixing ingredients 13 to 17 until uniform, and step C of adding B to A, emulsifying, adding ingredients 11 and 12 to the emulsion, and mixing them until uniform, to form W/O sunscreen milk.

| | Ingredients | Amount (%) |
|---|---|---|
| 1. | 60% D5 solution of Polymer I | 1 |
| 2. | Phenyl-modified partially crosslinked dimethylpolysiloxane compound *1 | 3 |
| 3. | Alkyl-silicone branched polyether-modified silicone *2 | 2 |
| 4. | Decamethylcyclopentasiloxane | 20 |
| 5. | Diphenylsiloxyphenyltrimethicone *3 | 8 |
| 6. | Triethylhexanoin | 2 |
| 7. | 2-Ethylhexyl p-methoxycinnamate | 7.5 |
| 8. | Octocrylene | 2.5 |
| 9. | Hexyl 2-[4-(diethylamino)-2-hydroxy-benzoyl]benzoate | 1 |
| 10. | Hybrid silicone composite powder *4 | 0.5 |
| 11. | Microparticulate titanium oxide dispersion *5 | 5 |
| 12. | Microparticulate zinc oxide dispersion *6 | 10 |
| 13. | 1,3-butylene glycol | 3 |
| 14. | Ethanol | 6 |
| 15. | Sodium citrate | 0.2 |
| 16. | Sodium chloride | 0.5 |
| 17. | Purified water | balance |
| | | 100 |

*1 Phenyl-modified partially crosslinked dimethyl-polysiloxane compound: KSG-18A (crosslink 10-20%, diphenylsiloxyphenyltrimethicone 80-90%) by Shin-Etsu Chemical Co., Ltd.
*2 Alkyl-silicone branched polyether-modified silicone: KF-6038 by Shin-Etsu Chemical Co., Ltd.
*3 Diphenylsiloxyphenyltrimethicone: KF-56A by Shin-Etsu Chemical Co., Ltd.
*4 Hybrid silicone composite powder: KSP-100 by Shin-Etsu Chemical Co., Ltd.
*5 Microparticulate titanium oxide dispersion: SPD-T5 by Shin-Etsu Chemical Co., Ltd.
*6 Microparticulate zinc oxide dispersion: SPD-Z5 by Shin-Etsu Chemical Co., Ltd.

The W/O sunscreen milk delivered light spreading without squeaking, and light feel-on-use without powdery texture, and was satisfactorily water resistant and long lasting.

Example 5

W/O Sunscreen Milk

A cosmetic composition was prepared by step A of mixing ingredients 1 to 7 until uniform, step B of mixing ingredients 10 to 13 until uniform, and step C of adding B to A, emulsifying, adding ingredients 8 and 9 to the emulsion, and mixing them until uniform, to form W/O sunscreen milk.

| | Ingredients | Amount (%) |
|---|---|---|
| 1. | 80% D5 solution of Polymer II | 1 |
| 2. | Partially crosslinked polyether-modified silicone compound *1 | 2 |
| 3. | Partially crosslinked dimethylpolysiloxane compound *2 | 2 |
| 4. | Silicone branched polyether-modified silicone *3 | 1 |
| 5. | Dimethylpolysiloxane (6cs) | 5 |
| 6. | Decamethylcyclopentasiloxane | 3 |
| 7. | Isotridecyl isononanoate | 4 |
| 8. | Microparticulate titanium oxide dispersion *4 | 25 |
| 9. | Microparticulate zinc oxide dispersion *5 | 35 |

-continued

| | Ingredients | Amount (%) |
|---|---|---|
| 10. | Dipropylene glycol | 2 |
| 11. | Sodium citrate | 0.2 |
| 12. | Sodium chloride | 1 |
| 13. | Purified water | balance |
| | | 100 |

*1 Partially crosslinked polyether-modified silicone compound: KSG-210 (crosslink 2-30%, climethylpolysiloxane (6cs) 70-80%) by Shin-Etsu Chemical Co., Ltd.
*2 Partially crosslinked dimethylpolysiloxane compound: KSG-15 (crosslink 4-10%, decamethylcyclopentasiloxane 90-96%) by Shin-Etsu Chemical Co., Ltd.
*3 Silicone branched polyether-modified silicone: KF-6028 by Shin-Etsu Chemical Co., Ltd.
*4 Microparticulate titanium oxide dispersion: SPD-T5 by Shin-Etsu Chemical Co., Ltd.
*5 Microparticulate zinc oxide dispersion: SPD-Z5 by Shin-Etsu Chemical Co., Ltd.

The W/O sunscreen milk delivered light spreading without squeaking, and light feel-on-use without powdery texture, and was satisfactorily water resistant and long lasting.

Example 6

W/O Cream Foundation

A cosmetic composition was prepared by step A of dispersing ingredients 9 to 14 on a roll mill, step B of mixing ingredients 1 to 8 until uniform, step C of mixing ingredients 15 to 19 until uniform, and step D of adding C to B, emulsifying, adding A to the emulsion, to form W/O cream foundation.

| Ingredients | Amount (%) |
|---|---|
| 1. Alkyl-modified, partially crosslinked polyether-modified silicone compound *1 | 3.5 |
| 2. Alkyl-modified, partially crosslinked dimethylpolysiloxane compound *2 | 5 |
| 3. Alkyl branched polyether-modified silicone *3 | 3 |
| 4. Organo-modified clay mineral | 1.3 |
| 5. Decamethylcyclopentasiloxane | 20 |
| 6. 2-ethylhexyl p-methoxycinnamate | 7.5 |
| 7. 60% D5 solution of Polymer I | 1 |
| 8. Hybrid silicone composite powder *4 | 2 |
| 9. Triethylhexanoin | 7 |
| 10. Acrylic silicone base graft copolymer *5 | 0.2 |
| 11. Silicone-treated titanium oxide *6 | 8.5 |
| 12. Silicone-treated yellow iron oxide *6 | proper |
| 13. Silicone-treated red iron oxide *6 | proper |
| 14. Silicone-treated black iron oxide *6 | proper |
| 15. 1,3-butylene glycol | 5 |
| 16. Methyl p-hydroxybenzoate | 0.15 |
| 17. Sodium citrate | 0.2 |
| 18. Sodium chloride | 0.5 |
| 19. Purified water | balance |
| | 100 |

*1 Alkyl-modified, partially crosslinked polyether-modified silicone compound: KSG-330 (crosslink 15-25%, triethylhexanoin 75-85%) by Shin-Etsu Chemical Co., Ltd.
*2 Alkyl-modified, partially crosslinked dimethylpolysiloxane compound: KSG-43 (crosslink 25-35%, triethylhexanoin 65-75%) by Shin-Etsu Chemical Co., Ltd.
*3 Alkyl branched polyether-modified silicone: KF-6048 by Shin-Etsu Chemical Co., Ltd.
*4 Hybrid silicone composite powder: KSP-100 by Shin-Etsu Chemical Co., Ltd.
*5 Acrylic silicone base graft copolymer: KP-578 by Shin-Etsu Chemical Co., Ltd.
*6 Silicone-treated powder: powders surface treated with KF-9909 by Shin-Etsu Chemical Co., Ltd. to be hydrophobic The W/O cream foundation was free of squeakiness, light spreading, long lasting, and non-secondary-sticking.

Example 7

W/O Liquid Foundation

A cosmetic composition was prepared by step A of dispersing ingredients 8 to 13 on a roll mill, step B of mixing ingredients 1 to 7 until uniform, step C of mixing ingredients 14 to 19 until uniform, and step D of adding C to B, emulsifying, adding A to the emulsion, to form W/O liquid foundation.

| | Ingredients | Amount (%) |
|---|---|---|
| 1. | Partially crosslinked polyether-modified silicone compound *1 | 3.5 |
| 2. | Alkyl branched polyether-modified silicone *2 | 3 |
| 3. | Phenyl-modified partially crosslinked dimethyl-polysiloxane compound *3 | 5 |
| 4. | Organo-modified clay mineral | 1.5 |
| 5. | Diphenylsiloxyphenyltrimethicone *4 | 6 |
| 6. | Decamethylcyclopentasiloxane | 18 |
| 7. | Isotridecyl isononanoate | 7.5 |
| 8. | 60% solution of Polymer I in dimethicone (6cs) | 1 |
| 9. | Metal soap-treated microparticulate titanium oxide with average primary particle size 20 nm | 5 |
| 10. | Silicone-treated titanium oxide *5 | 6.5 |
| 11. | Silicone-treated yellow iron oxide *5 | proper |
| 12. | Silicone-treated red iron oxide *5 | proper |
| 13. | Silicone-treated black iron oxide *5 | proper |
| 14. | Glycerol | 2 |
| 15. | Dipropylene glycol | 3 |
| 16. | Phenoxyethanol | 0.2 |
| 17. | Sodium citrate | 0.2 |
| 18. | Sodium chloride | 0.5 |
| 19. | Purified water | balance |
| | | 100 |

*1 Partially crosslinked polyether-modified silicone compound: KSG-210 (crosslink 20-30%, dimethylpolysiloxane (6cs) 70-80%) by Shin-Etsu Chemical Co., Ltd.
*2 Alkyl branched polyether-modified silicone: KF-6048 by Shin-Etsu Chemical Co., Ltd.
*3 Phenyl-modified, partially crosslinked dimethyl-polysiloxane compound: KSG-18A (crosslink 10-20%, diphenylsiloxyphenyltrimethicone 80-90%) by Shin-Etsu Chemical Co., Ltd.
*4 Diphenylsiloxyphenyltrimethicone: KF-56A by Shin-Etsu Chemical Co., Ltd.
*5 Silicone-treated powder: powders surface treated with KF-9909 by Shin-Etsu Chemical Co., Ltd. to be hydrophobic The W/O liquid foundation was free of squeakiness, light spreading, long lasting, and non-secondary-sticking.

Example 8

W/O Stick Foundation

A cosmetic composition was prepared by step A of dispersing ingredients 10 to 14 on a roll mill, step B of heating ingredients 1 to 9 at 95° C. and mixing them until uniform, step C of mixing A and ingredients 15 to 17 until uniform and heating at 85° C., and step D of adding C to B, emulsifying, filling a stick container with the emulsion, and allowing the emulsion to slowly cool down, to form W/O stick foundation.

| | Ingredients | Amount (%) |
|---|---|---|
| 1. | Partially crosslinked polyglycerol-modified silicone compound *1 | 4 |
| 2. | 60% solution of Polymer Tin dimethicone (6cs) | 1 |
| 3. | Alkyl-silicone branched polyether-modified silicone *2 | 1.5 |
| 4. | Inulin stearate *3 | 2 |
| 5. | Ceresin | 6 |
| 6. | Neopentyl glycol diethylhexanoate | 8 |
| 7. | Triethylhexanoin | 8 |
| 8. | Dimethylpolysiloxane (6cs) | 7 |
| 9. | Polymethylsilsequioxane *4 | 1.5 |
| 10. | Silicone-treated titanium oxide *5 | 6.5 |
| 11. | Silicone-treated yellow iron oxide *5 | proper |
| 12. | Silicone-treated red iron oxide *5 | proper |
| 13. | Silicone-treated black iron oxide *5 | proper |
| 14. | Monooleic acid polyoxyethylene sorbitan (20 E.O.) | 0.3 |
| 15. | Dipropylene glycol | 5 |
| 16. | Methyl p-hydroxybenzoate | 0.1 |
| 17. | Purified water | balance |
| | | 100 |

*1 Partially crosslinked polyglycerol-modified silicone compound: KSG-710 (crosslink 20-30%, dimethylpolysiloxane (6cs) 70-80%) by Shin-Etsu Chemical Co., Ltd.
*2 Alkyl-silicone branched polyether-modified silicone: KF-6038 by Shin-Etsu Chemical Co., Ltd.
*3 Inulin stearate: Rheopearl ISK2 by Chiba Flour Milling Co., Ltd.
*4 Polymethylsilsesquioxane: KMP-590 by Shin-Etsu Chemical Co., Ltd.
*5 Silicone-treated powder: powders surface treated with KF-9909 by Shin-Etsu Chemical Co., Ltd. to be hydrophobic The W/O stick foundation was non-squeaking, light spreading, long lasting, and non-secondary-sticking.

Example 9

Lipstick

A cosmetic composition was prepared by step A of dispersing ingredients 9 to 16 on a roll mill, step B of heating ingredients 1 to 8 at 95° C. and mixing them until uniform, step C of mixing A, B and ingredients 17 to 18 until uniform and heating at 85° C., and step D of filling a stick container with C to form a lipstick.

| | Ingredients | Amount (%) |
|---|---|---|
| 1. | Polyethylene | 7 |
| 2. | Microcrystalline wax | 3 |
| 3. | Silicone wax *1 | 10.5 |
| 4. | Triethylhexanoin | 14 |
| 5. | Neopentyl glycol diethylhexanoate | 14 |
| 6. | Neopentyl glycol dicaprylate | 8 |
| 7. | Hydrogenated polyisobutene | balance |
| 8. | Diphenyl dimethicone *2 | 7.5 |
| 9. | Sericite | 0.7 |
| 10. | Red #201 | proper |
| 11. | Red #202 | proper |
| 12. | Yellow #4 | proper |
| 13. | Silicone-treated titanium oxide *3 | 2.7 |
| 14. | Silicone-treated black iron oxide *3 | proper |
| 15. | Silicone-treated red iron oxide *3 | proper |
| 16. | Polyglyceryl triisostearate | 24 |
| 17. | Mica | 6 |
| 18. | 60% D5 solution of Polymer I | 1 |
| | | 100 |

*1 Silicone wax: KP-561P by Shin-Etsu Chemical Co., Ltd.
*2 Diphenyl dimethicone: KF-54HV by Shin-Etsu Chemical Co., Ltd.
*3 Silicone-treated powder: powders surface treated with KF-574 by Shin-Etsu Chemical Co., Ltd. to be hydrophobic The lipstick was free of squeakiness, unctuous texture, oozing, and secondary sticking, and was long lasting.

Example 10

Eye Cream

A cosmetic composition was prepared by step A of mixing ingredients 1 to 7 until uniform, step B of mixing ingredients 8 to 12 until uniform, and step C of adding B to A and emulsifying to form an eye cream.

| | Ingredients | Amount (%) |
|---|---|---|
| 1. | Silicone alkyl-modified, partially crosslinked polyether-modified silicone compound *1 | 4 |

-continued

| | Ingredients | Amount (%) |
|---|---|---|
| 2. | Silicone alkyl-modified, partially crosslinked dimethylpolysiloxane compound *2 | 6 |
| 3. | Silicone alkyl branched polyether-modified silicone *3 | 0.5 |
| 4. | Squalane | 15 |
| 5. | Jojoba oil | 3 |
| 6. | 60% D5 solution of Polymer I | 2 |
| 7. | Alkyl-modified hybrid silicone composite powder *4 | 1.5 |
| 8. | 1,3-butylene glycol | 7 |
| 9. | Phenoxyethanol | 0.25 |
| 10. | Sodium citrate | 0.2 |
| 11. | Sodium chloride | 0.5 |
| 12. | Purified water | balance |
| | | 100 |

*1 Silicone alkyl-modified, partially crosslinked polyether-modified silicone compound: KSG-350Z (crosslink 20-30%, cyclopentasiloxane 70-80%) by Shin-Etsu Chemical Co., Ltd.
*2 Silicone alkyl-modified, partially crosslinked dimethylpolysiloxane compound: KSG-045Z (crosslink 15-25%, cyclopentasiloxane 75-85%) by Shin-Etsu Chemical Co., Ltd.
*3 Silicone alkyl branched polyether-modified silicone: KF-6038 by Shin-Etsu Chemical Co., Ltd.
*4 Alkyl-modified hybrid silicone composite powder: KSP-441 by Shin-Etsu Chemical Co., Ltd.

The eye cream was free of squeakiness and unctuous texture, delivered dry feel and light spreading, and remained resilient.

Example 11

Wrinkle Concealer

A cosmetic composition was prepared by step A of mixing ingredients 1 to 6 until uniform and step B of adding ingredient 7 to A and mixing to form a wrinkle concealer.

| | Ingredients | Amount (%) |
|---|---|---|
| 1. | Partially crosslinked polyether-modified silicone compound *1 | 3 |
| 2. | Partially crosslinked dimethylpolysiloxane compound *2 | 55 |
| 3. | Partially crosslinked dimethylpolysiloxane compound *3 | 15 |
| 4. | Decamethylcyclopentasiloxane | balance |
| 5. | Highly polymerized dimethylpolysiloxane/D5 mixture *4 | 5 |
| 6. | 80% D5 solution of Polymer II | 2 |
| 7. | Hybrid silicone composite powder *5 | 12 |
| | | 100 |

*1 Partially crosslinked polyether-modified silicone compound: KSG-210 (crosslink 20-30%, dimethylpolysiloxane (6cs) 70-80%) by Shin-Etsu Chemical Co., Ltd.
*2 Partially crosslinked dimethylpolysiloxane compound: KSG-15 (crosslink 4-10%, D5 90-96%) by Shin-Etsu Chemical Co., Ltd.
*3 Partially crosslinked dimethylpolysiloxane compound: KSG-16 (crosslink 20-30%, dimethylpolysiloxane (6cs) 70-80%) by Shin-Etsu Chemical Co., Ltd.
*4 Highly polymerized dimethylpolysiloxane/D5 mixture: KF-9028 by Shin-Etsu Chemical Co., Ltd.
*5 Hybrid silicone composite powder: KSP-101 by Shin-Etsu Chemical Co., Ltd.

The wrinkle concealer was free of squeakiness and unctuous texture, and delivered dry feel, light spreading, and lasting sealing effect.

Example 12

W/O Sunscreen Cream

A cosmetic composition was prepared by step A of mixing ingredients 1 to 8 until uniform, step B of mixing ingredients 9 to 15 until uniform, and step C of adding B to A and emulsifying to form a sunscreen cream.

| | Ingredients | Amount (%) |
|---|---|---|
| 1. | Alkyl-modified, partially crosslinked polyglycerol-modified silicone compound *1 | 3 |
| 2. | Alkyl-modified, partially crosslinked dimethylpolysiloxane compound *2 | 3 |
| 3. | Silicone alkyl branched polyglycerol-modified silicone *3 | 1.5 |
| 4. | Diphenylsiloxyphenyltrimethicone *4 | 12 |
| 5. | 2-ethylhexyl p-methoxycinnamate | 6 |
| 6. | Octyl salicylate | 1 |
| 7. | Hybrid silicone composite powder *5 | 3 |
| 8. | 60% D5 solution of Polymer I | 2 |
| 9. | Xanthan gum | 0.3 |
| 10. | Dipropylene glycol | 5 |
| 11. | Glycerol | 3 |
| 12. | Methyl p-hydroxybenzoate | 0.1 |
| 13. | Sodium citrate | 0.2 |
| 14. | Sodium chloride | 0.5 |
| 15. | Purified water | balance |
| | | 100 |

*1 Alkyl-modified, partially crosslinked polyglycerol-modified silicone compound: KSG-840 (crosslink 25-35%, squalane 65-75%) by Shin-Etsu Chemical Co., Ltd.
*2 Alkyl-modified, partially crosslinked dimethylpolysiloxane compound: KSG-43 (crosslink 25-35%, triethylhexanoin 65-75%) by Shin-Etsu Chemical Co., Ltd.
*3 Silicone alkyl branched polyglycerol-modified silicone: KF-6105 by Shin-Etsu Chemical Co., Ltd.
*4 Diphenylsiloxyphenyltrimethicone: KF-56A by Shin-Etsu Chemical Co., Ltd.
*5 Hybrid silicone composite powder: KSP-105 by Shin-Etsu Chemical Co., Ltd.

The W/O sunscreen cream delivered light spreading without squeaking, and light feel-on-use without unctuous texture, and was water resistant and long lasting.

Example 13

O/W Sunscreen Cream

A cosmetic composition was prepared by step A of heating ingredients 1 to 5 at 80° C. and mixing them until uniform, step B of heating ingredients 6 to 13 at 80° C. and mixing them until uniform, and step C of adding B to A, emulsifying, allowing the emulsion to cool down slowly, adding ingredient 14, and mixing until uniform, to form a sunscreen cream.

| | Ingredients | Amount (%) |
|---|---|---|
| 1. | Xanthan gum | 0.2 |
| 2. | 1,3-butylene glycol | 8 |
| 3. | Methyl p-hydroxybenzoate | 0.1 |
| 4. | Sodium acrylate-sodium acryloyhdimethyltaurate copolymer compound *1 | 2 |
| 5. | Purified water | balance |
| 6. | 60% D5 solution of Polymer I | 0.3 |
| 7. | Diphenylsiloxyphenyltrimethicone *2 | 3 |
| 8. | Partially crosslinked dimethylpolysiloxane compound *3 | 1.5 |
| 9. | Cetanol | 2 |
| 10. | 2-ethylhexyl p-methoxycinnamate | 5 |
| 11. | 2,4-bis[14-(2-ethylhexyloxy)-2-hydroxylphenyl]-6-(4-methoxyphenyl)-1,3,5-triazine | 1 |
| 12. | Polyoxyethylene(60) hardened castor oil | 1 |
| 13. | Polyether-modified silicone *4 | 0.5 |
| 14. | Ethanol | 10 |
| | | 100 |

*1 Sodium acrylate-sodium acryloyklimethyltaurate copolymer compound: SIMULGEL EG (crosslink 35-40%) by SEPPIC
*2 Diphenylsilovphenyltrimethicone: KF-56A by Shin-Etsu Chemical Co., Ltd.
*3 Partially crosslinked dimethylpolysiloxane compound: KSG-016F (crosslink 20-30%, dimethylpolysiloxane (6cs) 70-80%) by Shin-Etsu Chemical Co., Ltd.
*4 Polyether-modified silicone: KF-6011 by Shin-Etsu Chemical Co., Ltd.

The O/W sunscreen cream delivered light spreading without squeaking, and light feel-on-use without unctuous texture, and was water resistant and long lasting.

Example 14

Mousse Cheek

A cosmetic composition was prepared by step A of heating ingredients 1 to 6 at 80° C. and mixing them until uniform, step B of mixing ingredients 7 to 12 on a Henschel mixer until uniform, and step C of adding B to A and cooling down slowly, to form a mousse cheek.

|    | Ingredients | Amount (%) |
|----|-------------|------------|
| 1. | Partially crosslinked dimethylpolysiloxane compound *1 | 28 |
| 2. | Decamethylcyclopentasiloxane | balance |
| 3. | Neopentyl glycol diisostearate | 4 |
| 4. | Inulin stearate *2 | 10 |
| 5. | Amorphous silicic anhydride *3 | 0.5 |
| 6. | 60% D5 solution of Polymer I | 5 |
| 7. | Silicone-treated titanium oxide *4 | 0.2 |
| 8. | Red #202 | proper |
| 9. | Silicone-treated yellow iron oxide *4 | proper |
| 10. | Silicone-treated black iron oxide *4 | proper |
| 11. | Silicone-treated mica *4 | 5.4 |
| 12. | Silicone-treated sericite *4 | 14 |
|    |             | 100 |

*1 Partially crosslinked dimethylpolysiloxane compound: KSG-16 (crosslink 20-30%, dimethylpolysiloxane (6cs) 70-80%) by Shin-Etsu Chemical Co., Ltd.
*2 Inulin stearate: Rheopearl KL2 by Chiba Flour Milling Co., Ltd.
*3 Amorphous silicic anhydride: AEROSIL 200 by Nippon Aerosil Co., Ltd.
*4 Silicone-treated powder: powders surface treated with KF-9901 by Shin-Etsu Chemical Co., Ltd. to be hydrophobic The mousse cheek was free of squeaking and unctuous texture, delivered light spreading, and was adherent and long lasting.

Example 15

Gel Eye Color

A cosmetic composition was prepared by step A of heating ingredients 1 to 5 at 80° C. and mixing them until uniform, step B of adding ingredients 6 to 9 to A, heating at 90° C., and mixing them until uniform, and step C of casting the mix into a container, to form a gel eye color.

|    | Ingredients | Amount (%) |
|----|-------------|------------|
| 1. | Partially crosslinked dimethylpolysiloxane compound *1 | 9 |
| 2. | Squalane | 15 |
| 3. | Dextrin palmitate *2 | 9 |
| 4. | Isotridecyl isononanoate | balance |
| 5. | 60% D5 solution of Polymer I | 2 |
| 6. | Amorphous silicic anhydride *3 | 0.1 |
| 7. | Hybrid silicone composite powder *4 | 5 |
| 8. | Barium sulfate | 10 |
| 9. | Silicone treated mica *5 | 30 |
|    |             | 100 |

*1 Partially crosslinked dimethylpolysiloxane compound: KSG-16 (crosslink 20-30%, dimethylpolysiloxane (6cs) 70-80%) by Shin-Etsu Chemical Co., Ltd.
*2 Dextrin palmitate: Rheopearl KL2 by Chiba Flour Milling Co., Ltd.
*3 Amorphous silicic anhydride: AEROSIL 972 by Nippon Aerosil Co., Ltd.
*4 Hybrid silicone composite powder: KSP-102 by Shin-Etsu Chemical Co., Ltd.
*5 Silicone-treated powder: powder surface treated with KP-574 by Shin-Etsu Chemical Co., Ltd. to be hydrophobic The gel eye color delivered light spreading without unctuous or powdery texture, and was long lasting.

Example 16

Powder Foundation

A cosmetic composition was prepared by step A of mixing ingredients 1 to 4 until uniform, step B of mixing ingredients 5 to 13 until uniform, and step C of adding A to B, mixing them on a Henschel mixer until uniform, passing the powder through a mesh, compacting the powder in a metal pan with the aid of a mold, to form a powder foundation.

|    | Ingredients | Amount (%) |
|----|-------------|------------|
| 1. | 2-ethylhexyl p-methoxycinnamate | 4 |
| 2. | Diphenylsiloxyphenyltrimethicone *1 | 4.5 |
| 3. | Triethylhexanoin | 1.5 |
| 4. | 60% D5 solution of Polymer I | 1 |
| 5. | Barium sulfate | 10 |
| 6. | Phenyl-modified hybrid silicone composite powder *2 | 5 |
| 7. | Polymethylsilsesquioxane *3 | 4 |
| 8. | Silicone-treated mica *4 | 30 |
| 9. | Silicone-treated talc *4 | balance |
| 10. | Silicone-treated titanium oxide *4 | 6 |
| 11. | Silicone-treated yellow iron oxide *4 | proper |
| 12. | Silicone-treated red iron oxide *4 | proper |
| 13. | Silicone-treated black iron oxide *4 | proper |
|    |             | 100 |

*1 Diphenylsiloxyphenyltrimethicone: KF-56A by Shin-Etsu Chemical Co., Ltd.
*2 Phenyl-modified hybrid silicone composite powder: KSP-300 by Shin-Etsu Chemical Co., Ltd.
*3 Polymethylsilsesquioxane: KMP-590 by Shin-Etsu Chemical Co., Ltd.
*4 Silicone-treated powder: powders surface treated with KP-574 by Shin-Etsu Chemical Co., Ltd. to be hydrophobic The powder foundation was light spreading, lasting and non-secondary-sticking.

Example 17

Out-Bath Hair Treatment

A cosmetic composition was prepared by step A of mixing ingredients 1 to 4 until uniform, step B of mixing ingredients 6 to 11 until uniform, and step C of adding B to A, emulsifying, adding ingredient 5 to the emulsion to form an out-bath hair treatment.

|    | Ingredients | Amount (%) |
|----|-------------|------------|
| 1. | 60% dimethicone (6cs) solution of Polymer I | 3 |
| 2. | Partially crosslinked dimethylpolysiloxane compound *1 | 1 |
| 3. | Branched polyether-modified silicone *2 | 0.2 |
| 4. | Dimethylpolysiloxane (6cs) | 8.5 |
| 5. | Perfume | proper |
| 6. | Dipropylene glycol | 8 |
| 7. | Ethanol | 5 |
| 8. | Methyl p-hydroxybenzoate | 0.1 |
| 9. | Sodium citrate | 0.2 |
| 10. | Sodium chloride | 0.5 |
| 11. | Purified water | balance |
|    |             | 100 |

*1 Partially crosslinked dimethylpolysiloxane compound: KSG-19 (crosslink 10-20%, dimethylpolysiloxane (6cs) 80-90%) by Shin-Etsu Chemical Co., Ltd.
*2 Branched polyether-modified silicone: KF-6017 by Shin-Etsu Chemical Co., Ltd.

The out-bath hair treatment delivered light spreading and imparted luster and smoothness to the hair.

Example 18

Hair Treatment

A cosmetic composition was prepared by step A of heating ingredients 1 to 6 at 70° C. and mixing until uniform, step B of heating ingredients 7 to 9 at 70° C. and mixing until uniform, and step C of adding B to A, emulsifying, slowly cooling, adding ingredients 10 and 11 to the emulsion to form a hair treatment.

| | Ingredients | Amount (%) |
|---|---|---|
| 1. | 60% dimethicone (6cs) solution of Polymer I | 0.4 |
| 2. | Cetanol | 2 |
| 3. | Cetyl octanoate | 2.5 |
| 4. | Behentrimonium chloride | 1 |
| 5. | Butyl p-hydroxybenzoate | 0.1 |
| 6. | Diphenylsiloxyphenyltrimethicone *1 | 1.5 |
| 7. | Propylene glycol | 5 |
| 8. | Hydroxyethyl cellulose | 0.1 |
| 9. | Purified water | balance |
| 10. | Amino-modified silicone emulsion *2 | 4 |
| 11. | Perfume | proper |
| | | 100 |

*1 Diphenylsiloxyphenyltrimethicone: KF-56A by Shin-Etsu Chemical Co., Ltd.
*2 Amino-modified silicone emulsion: X-52-2328 by Shin-Etsu Chemical Co., Ltd.

The hair treatment delivered light spreading and imparted luster and smoothness to the hair. By furnishing the 60% dimethicone (6cs) solution of Polymer I as W/O emulsion like ingredient 10, formulation can be done in an easy and stable manner.

Example 19

Hair Oil

A cosmetic composition was prepared by mixing ingredients 1 to 7 until uniform, to form a hair oil.

| | Ingredients | Amount (%) |
|---|---|---|
| 1. | 60% dimethicone (6cs) solution of Polymer I | 2 |
| 2. | Diphenylsiloxyphenyltrimethicone *1 | 12 |
| 3. | Diethylhexyl succinate | 8 |
| 4. | Highly polymerized dimethylpolysiloxane blend solution *2 | 2 |
| 5. | Tocopherol | 0.1 |
| 6. | Perfume | 0.1 |
| 7. | Hydrogenated polyisobutene | balance |
| | | 100 |

*1 Diphenylsiloxyphenyltrimethicone: KF-56A by Shin-Etsu Chemical Co., Ltd.
*2 Highly polymerized dimethylpolysiloxane blend solution: KF-9030 by Shin-Etsu Chemical Co., Ltd.

The hair oil delivered light spreading and imparted luster and smoothness to the hair.

Example 20

Hair Wax

A cosmetic composition was prepared by step A of heating ingredients 10 to 16 at 80° C. and mixing until uniform, step B of heating ingredients 1 to 9 at 90° C. and mixing until uniform, step C of adding B to A, emulsifying, and cooling down to room temperature, and step D of adding ingredients 17 and 18 to C and mixing until uniform, to form a hair wax.

| | Ingredients | Amount (%) |
|---|---|---|
| 1. | 80% isododecane solution of Polymer II | 1 |
| 2. | Methyltrimethicone *1 | 10 |
| 3. | Candelilla wax | 13 |
| 4. | Microcrystalline wax | 8 |
| 5. | POE glyceryl isostearate | 2 |
| 6. | Glycerol monostearate | 3 |
| 7. | Polyether-modified silicone *2 | 2 |
| 8. | Stearic acid | 2 |
| 9. | 2-ethylhexyl p-methoxycinnamate | 0.1 |
| 10. | Propylene glycol | 6 |
| 11. | 1,3-butylene glycol | 6 |
| 12. | Carboxyvinyl polymer | 0.3 |
| 13. | Methyl p-hydroxybenzoate | 0.2 |
| 14. | Phenoxyethanol | 0.3 |
| 15. | Trisodium edetate | proper |
| 16. | Purified water | balance |
| 17. | Potassium hydroxide (10% solution) | proper |
| 18. | Perfume | proper |
| | | 100 |

*1 Methyltrimethicone: TMF-1.5 by Shin-Etsu Chemical Co., Ltd.
*2 Polyether-modified silicone: KF-6011 by Shin-Etsu Chemical Co., Ltd.

The hair wax was less squeaking, retentive and hair style lasting.

Example 21

Oily Mascara

A cosmetic composition was prepared by step A of heating ingredients 1 to 6 at 95° C. and mixing until uniform, step B of adding ingredients 7 to 14 to A, heating them at 90° C. and mixing until uniform, and step C of slowly cooling B, to form an oily mascara.

| | Ingredients | Amount (%) |
|---|---|---|
| 1. | 80% isododecane solution of Polymer II | 8 |
| 2. | Isododecane solution of trimethylsiloxysilicic acid *1 | 12 |
| 3. | Dextrin palmitate *2 | 2 |
| 4. | Paraffin wax | 6 |
| 5. | Microcrystalline wax | 7 |
| 6. | Isododecane | 30 |
| 7. | Organo-modified clay mineral | 5.5 |
| 8. | Silicone-treated black iron oxide *3 | 5 |
| 9. | Silicone-treated talc *3 | 5 |
| 10. | Hybrid silicone composite powder *4 | 5 |
| 11. | Polyether-modified silicone *5 | 1.2 |
| 12. | Propylene carbonate | 1.6 |
| 13. | Methyl p-hydroxybenzoate | 0.1 |
| 14. | Isododecane | balance |
| | | 100 |

*1 Isododecane solution of trimethylsiloxysilicic acid: X-21-5595 by Shin-Etsu Chemical Co., Ltd.
*2 Dextrin palmitate: Rheopearl TL2 by Chiba Flour Milling Co., Ltd.
*3 Silicone-treated powder: powders surface treated with KF-9909 by Shin-Etsu Chemical Co., Ltd. to be hydrophobic
*4 Hybrid silicone composite powder: KSP-105 by Shin-Etsu Chemical Co., Ltd.
*5 Polyether-modified silicone: KF-6017 by Shin-Etsu Chemical Co., Ltd.

The oily mascara was good in finish, long lasting and retentive. By using a hard brittle coating of trimethylsiloxysilicic acid in combination, coating properties and feel-on-use such as finish may be adjusted.

Example 22

W/O Mascara

A cosmetic composition was prepared by step A of heating ingredients 1 to 8 at 95° C. and mixing until uniform, step B of adding ingredients 9 to 14 to A, heating them at 85°

C. and mixing until uniform, step C of heating ingredients 15 to 17 at 85° C. and mixing until uniform, and step D of adding C to B, emulsifying, and slowly cooling, to form a W/O oily mascara.

|  | Ingredients | Amount (%) |
|---|---|---|
| 1. | 80% isododecane solution of Polymer II | 6 |
| 2. | Isododecane solution of acrylic silicone base graft copolymer *1 | 10 |
| 3. | Dextrin (palmitate/ethylhexanoate) *2 | 3 |
| 4. | Silicone wax *3 | 2 |
| 5. | Ceresin | 2.5 |
| 6. | Microcrystalline wax | 4.5 |
| 7. | Diphenylsiloxyphenyltrimethicone *4 | 3 |
| 8. | Isododecane | balance |
| 9. | Organo-modifier clay mineral | 4 |
| 10. | Silicone-treated black iron oxide *5 | 5 |
| 11. | Silicone-treated talc *5 | 4.5 |
| 12. | Amorphous silicic anhydride *6 | 2.7 |
| 13. | Silicone branched polyether-modified silicone *7 | 1 |
| 14. | Propylene carbonate | 1.3 |
| 15. | Phenoxyethanol | 0.2 |
| 16. | 1,3-butylene glycol | 1 |
| 17. | Purified water | 12.8 |
|  |  | 100 |

*1 Isododecane solution of acrylic silicone base graft copolymer: KP-550 by Shin-Etsu Chemical Co., Ltd.
*2 Dextrin (palmitate/ethylhexanoate): Rheopearl TT2 by Chiba Flour Milling Co., Ltd.
*3 Silicone wax: KP-562P by Shin-Etsu Chemical Co., Ltd.
*4 Diphenylsiloxyphenyltrimethicone: KF-56A by Shin-Etsu Chemical Co., Ltd.
*5 Silicone-treated powder: powders surface treated with KF-9901 by Shin-Etsu Chemical Co., Ltd. to be hydrophobic
*6 Amorphous silicic anhydride: AEROSIL 972 by Nippon Aerosil Co., Ltd.
*7 Silicone branched polyether-modified silicone: KF-6028 by Shin-Etsu Chemical Co., Ltd.

The W/O mascara was good in finish, long lasting and retentive. By using a hard brittle coating of trimethylsiloxysilicic acid or a flexible coating of silicone-modified acrylic polymer in combination, coating properties and feel-on-use such as finish may be adjusted.

Japanese Patent Application Nos. 2017-053099 and 2017-230439 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An organic group modified organosilicon resin having the average compositional formula (1), the resin being solid or liquid at 25° C., $$(R^1_3SiO_{1/2})_a(R^2_3SiO_{1/2})_b(R^3_3SiO_{1/2})_c(R^1_2SiO_{2/2})_d(R^1SiO_{3/2})_e(SiO_{4/2})_f \quad (1)$$

wherein $R^1$ is each independently a $C_1$-$C_{30}$ alkyl, aryl or aralkyl group or a halogen-, amino- or carboxyl-substituted form thereof, $R^2$ is each independently a polyoxyalkylene group having the formula (2):

$$-(CH_2)_2-C_lH_{2l}-O-(C_2H_4O)_g(C_3H_6O)_hR^4 \quad (2)$$

wherein $R^4$ is a substituted or unsubstituted monovalent hydrocarbon group or hydrogen, l, g and h each are an integer meeting: $0 \le l \le 15$, $0 \le g \le 200$, $0 \le h \le 200$, and $8 \le g+h \le 200$, or $R^1$, at least one $R^2$ is a polyoxyalkylene group of formula (2), $R^3$ is each independently a group having the formula (3), (4), (5) or (6):

$$-(CH_2)_2-C_mH_{2m}-(SiR^1_2O)i-SiR^1_3 \quad (3)$$

$$-(CH_2)_2-C_mH_{2m}-SiR^1_{j1}-(OSiR^1_3)_{3-j1} \quad (4)$$

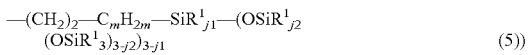

$$-(CH_2)_2-C_mH_{2m}-SiR^1_{j1}-(OSiR^1_{j2}(OSiR^1_3)_{3-j2})_{3-j1} \quad (5)$$

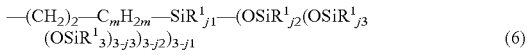

$$-(CH_2)_2-C_mH_{2m}-SiR^1_{j1}-(OSiR^1_{j2}(OSiR^1_{j3}(OSiR^1_3)_{3-j3})_{3-j2})_{3-j1} \quad (6)$$

wherein $R^1$ is as defined above, m, i and j1 to j3 each are an integer meeting: $0 \le m \le 5$, $0 \le i \le 500$, $0 \le j1 \le 2$, $0 \le j2 \le 2$, $0 \le j3 \le 2$, or $R^1$, at least one $R^3$ is a group of formula (3), (4), (5) or (6), a, b, c, d, e, and f each are a number meeting: $0 \le a \le 400$, $0 < b \le 200$, $0 < c \le 400$, $0 \le d \le 320$, $0 \le e \le 320$, $0 < f \le 1{,}000$, and $0.5 \le (a+b+c)/f \le 1.5$.

2. The organosilicon resin of claim 1, having a weight average molecular weight of 1,000 to 100,000.

3. The organosilicon resin of claim 1, having an HLB of 0.1 to 15 as calculated by the Griffin method.

4. The organosilicon resin of claim 1 wherein in formula (1), $1 \le c \le 400$, $0.3 \le c/b \le 100$, and $R^3$ contains at least a group of formula (3) wherein $0 < i \le 500$, the resin having an HLB of 0.1 to 5.5 as calculated by the Griffin method.

5. A method for preparing, the organic group-modified organosilicon resin of claim 1, comprising the step of effecting hydrosilylation reaction of a hydrosilyl-containing organosilicon resin having the average compositional formula (7), the resin being solid or liquid at 25° C.,

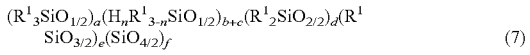

$$(R^1_3SiO_{1/2})_a(H_nR^1_{3-n}SiO_{1/2})_{b+c}(R^1_2SiO_{2/2})_d(R^1SiO_{3/2})_e(SiO_{4/2})_f \quad (7)$$

wherein $R^1$ is each independently a $C_1$-$C_{30}$ alkyl, aryl or aralkyl group or a halogen-, amino- or carboxyl-substituted form thereof, a, b, c, d, e, and f each are a number meeting: $0 \le a \le 400$, $0 < b \le 200$, $0 < c \le 400$, $0 \le d \le 320$, $0 \le e \le 320$, $0 < f \le 1{,}000$, and $0.5 \le (a+b+c)/f \le 1.5$, and n is an integer of 1 to 3, with at least one compound selected from an alkenyl-terminated compound having the formula (8), (9), (10), (11) and (12), and containing compound having the formula (8):

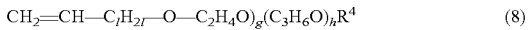

$$CH_2=CH-C_lH_{2l}-O-C_2H_4O)_g(C_3H_6O)_hR^4 \quad (8)$$

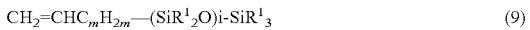

$$CH_2=CHC_mH_{2m}-(SiR^1_2O)i-SiR^1_3 \quad (9)$$

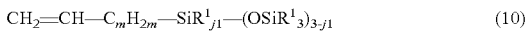

$$CH_2=CH-C_mH_{2m}-SiR^1_{j1}-(OSiR^1_3)_{3-j1} \quad (10)$$

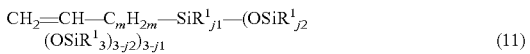

$$CH_2=CH-C_mH_{2m}-SiR^1_{j1}-(OSiR^1_{j2}(OSiR^1_3)_{3-j2})_{3-j1} \quad (11)$$

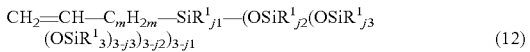

$$CH_2=CH-C_mH_{2m}-SiR^1_{j1}-(OSiR^1_{j2}(OSiR^1_{j3}(OSiR^1_3)_{3-j3})_{3-j2})_{3-j1} \quad (12)$$

wherein $R^4$ is a substituted or unsubstituted monovalent hydrocarbon group or hydrogen, l, g and h each are an integer meeting: $0 \le l \le 15$, $0 \le g \le 200$, $0 \le h \le 200$, and $8 \le g+h \le 200$, m, i and j1 to j3 each are an integer meeting: $0 \le m \le 5$, $0 \le i \le 500$, $0 \le j1 \le 2$, $0 \le j2 \le 2$, and $0 \le j3 \le 2$.

6. A cosmetic composition comprising the organic group-modified organosilicon resin of claim 1.

* * * * *